(12) United States Patent
Dattwyler et al.

(10) Patent No.: US 10,006,912 B2
(45) Date of Patent: Jun. 26, 2018

(54) PEPTIDES FOR DIAGNOSING LYME DISEASE

(71) Applicant: BIOPEPTIDES CORP., East Setauket, NY (US)

(72) Inventors: Raymond J. Dattwyler, East Setauket, NY (US); Paul M. Arnaboldi, Queens, NY (US)

(73) Assignee: Biopeptides LLC, Setauket, NY (US)

( * ) Notice: Subject to any disclaimer, the term of this patent is extended or adjusted under 35 U.S.C. 154(b) by 0 days. days.

(21) Appl. No.: 15/102,002

(22) PCT Filed: Dec. 8, 2014

(86) PCT No.: PCT/US2014/069165
§ 371 (c)(1),
(2) Date: Jun. 6, 2016

(87) PCT Pub. No.: WO2015/085323
PCT Pub. Date: Jun. 11, 2015

(65) Prior Publication Data
US 2016/0313326 A1 Oct. 27, 2016

Related U.S. Application Data

(60) Provisional application No. 61/912,675, filed on Dec. 6, 2013.

(51) Int. Cl.
*A61K 39/02* (2006.01)
*C07K 14/00* (2006.01)
(Continued)

(52) U.S. Cl.
CPC ........ *G01N 33/56911* (2013.01); *C07K 14/20* (2013.01); *G01N 2333/20* (2013.01); *G01N 2469/20* (2013.01); *G01N 2800/26* (2013.01)

(58) Field of Classification Search
CPC .... G01N 33/53; G01N 33/569; A01K 67/027; A61K 31/00; A61K 39/02; A61K 39/395;
(Continued)

(56) References Cited

U.S. PATENT DOCUMENTS 6,312,907 B1 11/2001 Guo et al.
6,517,838 B1 2/2003 Hook et al.
(Continued)

FOREIGN PATENT DOCUMENTS

CA        2 708 753    * 12/2011 ............. C07K 14/20
WO   WO 1997/027301   * 10/1996 ............. G01N 33/53
(Continued)

OTHER PUBLICATIONS

International Search Report dated Mar. 13, 2015 issued in corresponding PCT/US2014/069165 application (pp. 1-5).
(Continued)

*Primary Examiner* — Jana A Hines
(74) *Attorney, Agent, or Firm* — Millen White Zelano & Branigan, P.C.

(57) ABSTRACT

The present invention relates, e.g., to a composition comprising peptides represented by SEQ ID NO:1, or active variants thereof, wherein the peptides or active variants can bind specifically to an antibody induced by a causative agent of Lyme disease (a pathogenic *Borrelia*), e.g. in a sample from a subject having Lyme disease. Compositions of the invention may comprise multiple peptides, from multiple proteins. Diagnostic kits comprising the peptides are described, as are diagnostic assays using the peptides.

11 Claims, 3 Drawing Sheets

(51) Int. Cl.
*G01N 33/569* (2006.01)
*C07K 14/20* (2006.01)

(58) Field of Classification Search
CPC ........ A61K 48/00; A61K 38/00; A61K 39/00; A61P 31/00; C07K 14/20; C07K 16/12; C12N 1/21; C12N 15/09; C12N 15/30; C12Q 1/68
See application file for complete search history.

(56) References Cited

U.S. PATENT DOCUMENTS

| | | |
|---|---|---|
| 6,902,893 B1 | 6/2005 | Choi et al. |
| 2012/0142023 A1 | 6/2012 | Ascoli et al. |

FOREIGN PATENT DOCUMENTS

| | | | | |
|---|---|---|---|---|
| WO | WO 2000/078800 | * 12/2000 | ............. | A61K 39/02 |
| WO | WO 2011/163258 | * 12/2011 | ........... | G01N 33/569 |

OTHER PUBLICATIONS

Written Opinion of the International Searching Authority dated Mar. 13, 2015 issued in corresponding PCT/US2014/069165 application (pp. 1-6).

T. Heikkila et al., "Cloning of the Gene Encoding the Decorin-Binding Protein B (DbpB) in Borrelia Burgdorferi Sensu Lato and Characterisation of the Antibody Responses to DbpB in Lyme Borreliosis", Journal of Medical Microbiology, vol. 51, No. 8 (2002) pp. 641-648.

T. Heikkila et al., "Recombinant or Peptide Antigens in the Serology of Lyme Arthritis in Children", Journal of Infectious Diseases, vol. 187, No. 12 (2003) pp. 1888-1894.

Partial Supplementary Search Report corresponding to PCT/US2014/069165, dated Jun. 9, 2017.

* cited by examiner

|  |  | SEQ ID NO: |
|---|---|---|
| Borrelia burgdorferi B31 | KDLKNKILKIKKEATGKGVLFEAFTGLKTG | 1 |
| Borrelia burgdorferi ia | KDLKNKILKIKKEATGKGVLFEAFTGLKTG | 1 |
| Borrelia burgdorferi ZS7 | KDLKNKILKIKKEATGKGVLFEAFTGLKTG | 1 |
| Borrelia burgdorferi JD1 | KDLKNKILKIKKEATEKGVLFEAFTGLKTG | 24 |
| Borrelia burgdorferi N40 | KDLKNKILKIKKEATGKGVLFEAFTGLKTG | 1 |
| Borrelia burgdorferi IPS | KDLKNKILKIKKEATGKGVLFEAFTGLKTG | 1 |
| Borrelia burgdorferi Sh-2-82 | KDLKNKILKIKKDATGKGVLFEAFTGLKTG | 4 |
| Borrelia garinii Far04 | DNVKNKILQIKEEAAKKGVNFKAFTGTATG | 2 |
| Borrelia garinii PBr | DNVKNKILQIKEEAAKKGVNFKAFTGTATG | 2 |
| Borrelia garinii 46 | DNVKNKILQIKEEAAKKGVNFKAFTGTATG | 2 |
| Borrelia garinii Nsk-10-06 | DNVKNKILQIKEEAAKKGVNFKAFTGTATG | 2 |
| Borrelia afzelii | KDVKNKILQIKKDAEDKGVNFAAFTSSETG | 3 |
| Borrelia afzelii PKo | KDVKNKILQIKKDAEDKGVNFAAFTSSETG | 3 |
| Consensus | KDLKNKILKIKKEATGKGVLFEAFTGLKTG | 5 |

FIG. 2

SEQUENCE LISTING

```
<160> NUMBER OF SEQ ID NOS: 24

<210> SEQ ID NO 1
<211> LENGTH: 30
<212> TYPE: PRT
<213> ORGANISM: Borrelia burgdorferi

<400> SEQUENCE: 1

Lys Asp Leu Lys Asn Lys Ile Leu Lys Ile Lys Lys Glu Ala Thr Gly
1               5                   10                  15

Lys Gly Val Leu Phe Glu Ala Phe Thr Gly Leu Lys Thr Gly
            20                  25                  30

<210> SEQ ID NO 2
<211> LENGTH: 30
<212> TYPE: PRT
<213> ORGANISM: Borrelia garinii

<400> SEQUENCE: 2

Asp Asn Val Lys Asn Lys Ile Leu Gln Ile Lys Glu Glu Ala Ala Lys
1               5                   10                  15

Lys Gly Val Asn Phe Lys Ala Phe Thr Gly Thr Ala Thr Gly
            20                  25                  30

<210> SEQ ID NO 3
<211> LENGTH: 30
```

```
<212> TYPE: PRT
<213> ORGANISM: Borrelia afzelii

<400> SEQUENCE: 3

Lys Asp Val Lys Asn Lys Ile Leu Gln Ile Lys Lys Asp Ala Glu Asp
1               5                   10                  15

Lys Gly Val Asn Phe Ala Ala Phe Thr Ser Ser Glu Thr Gly
            20                  25                  30

<210> SEQ ID NO 4
<211> LENGTH: 30
<212> TYPE: PRT
<213> ORGANISM: Borrelia burgdorferi

<400> SEQUENCE: 4

Lys Asp Leu Lys Asn Lys Ile Leu Lys Ile Lys Lys Asp Ala Thr Gly
1               5                   10                  15

Lys Gly Val Leu Phe Glu Ala Phe Thr Gly Leu Lys Thr Gly
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Lys Asp Leu Lys Asn Lys Ile Leu Lys Ile Lys Lys Glu Ala Thr Gly
1               5                   10                  15

Lys Gly Val Leu Phe Glu Ala Phe Thr Gly Leu Lys Thr Gly
            20                  25                  30

<210> SEQ ID NO 6
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Asp Leu Lys Asn Lys Ile Leu Lys Ile Lys Lys Glu Ala Thr Gly
1               5                   10                  15

Lys Gly Val Leu Phe Glu Ala Phe Thr Gly Leu Lys Thr Gly Gly Gly
            20                  25                  30

Gly Met Lys Lys Asn Asp Gln Ile Val Ala Ala Ile Ala Leu Arg Gly
        35                  40                  45

Val Ala
    50

<210> SEQ ID NO 7
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Lys Asp Leu Lys Asn Lys Ile Leu Lys Ile Lys Lys Glu Ala Thr Gly
1               5                   10                  15
```

Lys Gly Val Leu Phe Glu Ala Phe Thr Gly Leu Lys Thr Gly Gly
            20                  25                  30

Gly Pro Phe Ile Leu Glu Ala Lys Val Arg Ala Thr Val Ala Glu
        35                  40                  45

<210> SEQ ID NO 8
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Lys Asp Leu Lys Asn Lys Ile Leu Lys Ile Lys Lys Glu Ala Thr Gly
1               5                   10                  15

Lys Gly Val Leu Phe Glu Ala Phe Thr Gly Leu Lys Thr Gly Gly
            20                  25                  30

Asn Lys Thr Phe Asn Asn Leu Leu Lys Leu Thr Ile Leu Val Asn Gly
            35                  40                  45

Gly Gly Thr Ile Leu Val Asn Leu Leu Ile Ser Cys Gly Leu Thr Gly
        50                  55                  60

Ala
65

<210> SEQ ID NO 9
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Lys Asp Leu Lys Asn Lys Ile Leu Lys Ile Lys Lys Glu Ala Thr Gly
1               5                   10                  15

Lys Gly Val Leu Phe Glu Ala Phe Thr Gly Leu Lys Thr Gly Gly
            20                  25                  30

Gly Asn Lys Thr Phe Asn Asn Leu Leu Lys Leu Thr Ile Leu Val Asn
            35                  40                  45

<210> SEQ ID NO 10
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Asn Val Lys Asn Lys Ile Leu Gln Ile Lys Glu Glu Ala Ala Lys
1               5                   10                  15

Lys Gly Val Asn Phe Lys Ala Phe Thr Gly Thr Ala Thr Gly Gly
            20                  25                  30

Gly Met Lys Lys Asn Asp Gln Ile Val Ala Ala Ile Ala Leu Arg Gly
            35                  40                  45

Val Ala
    50

<210> SEQ ID NO 11
<211> LENGTH: 48
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 11

Asp Asn Val Lys Asn Lys Ile Leu Gln Ile Lys Glu Glu Ala Ala Lys
1               5                   10                  15

Lys Gly Val Asn Phe Lys Ala Phe Thr Gly Thr Ala Thr Gly Gly Gly
            20                  25                  30

Gly Pro Phe Ile Leu Glu Ala Lys Val Arg Ala Thr Thr Val Ala Glu
        35                  40                  45

<210> SEQ ID NO 12
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Asn Val Lys Asn Lys Ile Leu Gln Ile Lys Glu Glu Ala Ala Lys
1               5                   10                  15

Lys Gly Val Asn Phe Lys Ala Phe Thr Gly Thr Ala Thr Gly Gly Gly
            20                  25                  30

Gly Asn Lys Thr Phe Asn Asn Leu Leu Lys Leu Thr Ile Leu Val Asn
        35                  40                  45

Gly Gly Gly Thr Ile Leu Val Asn Leu Leu Ile Ser Cys Gly Leu Thr
    50                  55                  60

Gly Ala
65

<210> SEQ ID NO 13
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Lys Asp Val Lys Asn Lys Ile Leu Gln Ile Lys Lys Asp Ala Glu Asp
1               5                   10                  15

Lys Gly Val Asn Phe Ala Ala Phe Thr Ser Ser Glu Thr Gly Gly Gly
            20                  25                  30

Gly Met Lys Lys Asn Asp Gln Ile Val Ala Ile Ala Leu Arg Gly
        35                  40                  45

Val Ala
    50

<210> SEQ ID NO 14
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Lys Asp Val Lys Asn Lys Ile Leu Gln Ile Lys Lys Asp Ala Glu Asp
1               5                   10                  15
```

```
Lys Gly Val Asn Phe Ala Ala Phe Thr Ser Ser Glu Thr Gly Gly
            20                  25                  30

Gly Pro Phe Ile Leu Glu Ala Lys Val Arg Ala Thr Thr Val Ala Glu
            35                  40                  45

<210> SEQ ID NO 15
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Lys Asp Val Lys Asn Lys Ile Leu Gln Ile Lys Lys Asp Ala Glu Asp
1               5                   10                  15

Lys Gly Val Asn Phe Ala Ala Phe Thr Ser Ser Glu Thr Gly Gly Gly
            20                  25                  30

Asn Lys Thr Phe Asn Asn Leu Leu Lys Leu Thr Ile Leu Val Asn Gly
            35                  40                  45

Gly Gly Thr Ile Leu Val Asn Leu Leu Ile Ser Cys Gly Leu Thr Gly
        50                  55                  60

Ala
65

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys or Asp
<220> FEATURE:
<221> NAME/KEY: MOD_RES
<222> LOCATION: (2)..(2)
<223> OTHER INFORMATION: Asp or Asn
<220> FEATURE:
<221> NAME/KEY: MOD_RES
<222> LOCATION: (3)..(3)
<223> OTHER INFORMATION: Leu or Val
<220> FEATURE:
<221> NAME/KEY: MOD_RES
<222> LOCATION: (9)..(9)
<223> OTHER INFORMATION: Lys or Gln
<220> FEATURE:
<221> NAME/KEY: MOD_RES
<222> LOCATION: (12)..(12)
<223> OTHER INFORMATION: Lys or Glu
<220> FEATURE:
<221> NAME/KEY: MOD_RES
<222> LOCATION: (13)..(13)
<223> OTHER INFORMATION: Lys or Asp
<220> FEATURE:
<221> NAME/KEY: MOD_RES
<222> LOCATION: (15)..(15)
<223> OTHER INFORMATION: Thr, Ala or Glu
<220> FEATURE:
<221> NAME/KEY: MOD_RES
<222> LOCATION: (16)..(16)
<223> OTHER INFORMATION: Gly, Glu, Lys or Asp
<220> FEATURE:
<221> NAME/KEY: MOD_RES
<222> LOCATION: (20)..(20)
<223> OTHER INFORMATION: Leu or Asn
<220> FEATURE:
<221> NAME/KEY: MOD_RES
<222> LOCATION: (22)..(22)
```

```
<223> OTHER INFORMATION: Glu or Lys
<220> FEATURE:
<221> NAME/KEY: MOD_RES
<222> LOCATION: (26)..(26)
<223> OTHER INFORMATION: Gly or Ser
<220> FEATURE:
<221> NAME/KEY: MOD_RES
<222> LOCATION: (27)..(27)
<223> OTHER INFORMATION: Leu, Ser or Thr
<220> FEATURE:
<221> NAME/KEY: MOD_RES
<222> LOCATION: (28)..(28)
<223> OTHER INFORMATION: Lys, Ala or Glu

<400> SEQUENCE: 16

Xaa Xaa Xaa Lys Asn Lys Ile Leu Xaa Ile Lys Xaa Xaa Ala Xaa Xaa
1               5                   10                  15

Lys Gly Val Xaa Phe Xaa Ala Phe Thr Xaa Xaa Xaa Thr Gly
            20                  25                  30

<210> SEQ ID NO 17
<211> LENGTH: 13
<212> TYPE: PRT
<213> ORGANISM: Borrelia sp.

<400> SEQUENCE: 17

Val Gln Glu Gly Val Gln Gln Glu Gly Ala Gln Gln Pro
1               5                   10

<210> SEQ ID NO 18
<211> LENGTH: 10
<212> TYPE: PRT
<213> ORGANISM: Borrelia sp.

<400> SEQUENCE: 18

Pro Val Val Ala Glu Ser Pro Lys Lys Pro
1               5                   10

<210> SEQ ID NO 19
<211> LENGTH: 26
<212> TYPE: PRT
<213> ORGANISM: Borrelia sp.

<400> SEQUENCE: 19

Cys Met Lys Lys Asp Asp Gln Ile Ala Ala Ala Met Val Leu Arg Gly
1               5                   10                  15

Met Ala Lys Asp Gly Gln Phe Ala Leu Lys
            20                  25

<210> SEQ ID NO 20
<211> LENGTH: 17
<212> TYPE: PRT
<213> ORGANISM: Borrelia sp.
<220> FEATURE:
<221> NAME/KEY: MOD_RES
<222> LOCATION: (8)..(8)
<223> OTHER INFORMATION: Val or Gly

<400> SEQUENCE: 20

Met Lys Lys Asn Asp Gln Ile Xaa Ala Ala Ile Ala Leu Arg Gly Val
1               5                   10                  15

Ala

<210> SEQ ID NO 21
<211> LENGTH: 14
<212> TYPE: PRT
```

```
<213> ORGANISM: Borrelia sp.

<400> SEQUENCE: 21

Ile Leu Met Thr Leu Phe Leu Phe Ile Ser Cys Asn Asn Ser
1               5                   10

<210> SEQ ID NO 22
<211> LENGTH: 17
<212> TYPE: PRT
<213> ORGANISM: Borrelia sp.

<400> SEQUENCE: 22

Met Lys Lys Asp Asp Gln Ile Ala Ala Ala Ile Ala Leu Arg Gly Met
1               5                   10                  15

Ala

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 30
<212> TYPE: PRT
<213> ORGANISM: Borrelia burgdorferi

<400> SEQUENCE: 24

Lys Asp Leu Lys Asn Lys Ile Leu Lys Ile Lys Lys Glu Ala Thr Glu
1               5                   10                  15

Lys Gly Val Leu Phe Glu Ala Phe Thr Gly Leu Lys Thr Gly
            20                  25                  30
```

PEPTIDES FOR DIAGNOSING LYME DISEASE

This application claims the benefit of the filing date of U.S. Provisional Application 61/912,675, filed Dec. 6, 2013, which is incorporated by reference in its entirety herein.

This application was made with U.S. government support under Grant Nos. R44 AI074092 and R43 AI102435 by NIH-NIAID. Therefore, the government has certain rights in the invention.

SEQUENCE LISTING

The instant patent application contains a Sequence Listing which has been submitted via EFS-Web and is hereby incorporated by reference in its entirety. Said ASCII copy, created on Dec. 5, 2014, is named 64557-376058_SL.txt and is 11,085 bytes in size.

FIELD OF THE INVENTION

This invention relates, e.g., to agents and methods for diagnosing Lyme disease.

BACKGROUND INFORMATION

Lyme disease (sometimes referred to herein as LD or Lyme borreliosis) is a common vector-borne disease that is a significant public health concern. The disease is transmitted by the bite of various species of *Ixodes* ticks carrying the etiologic agent, a pathogenic *Borrelia* bacterium (a spirochete). Organisms of the *Borrelia burgdorferi* sensu lato group belong to the family Spirochaetaceae, genus *Borrelia*. There are at least 11 species in the *B. burgdorferi* complex and an unknown but large number of substrains. At least three genospecies of the *Borrelia burgdorferi* sensu lato group have been identified as pathogens: *B. burgdorferi* sensu stricto, *B. afzelii*, and *B. garinii*. In addition, other species of *Borrelia* have been implicated as being causative pathogenic agents. The major reservoir of the infection in the United States is the white footed mouse, and the infection can be transmitted to many mammalian species, including various other forms of wildlife, e.g. Eastern chipmunks, and dogs, cats, and humans.

Clinically, Lyme disease is a progressive disease with a wide array of manifestations. Early diagnosis and treatment is critical to prevent progression. Late disseminated infection can be associated with permanent damage to the nervous and musculoskeletal systems. Unlike most bacterial diseases that can be defined microbiologically by direct observation or culture of the pathogen, *B. burgdorferi* is difficult to culture or observe in clinical samples. Therefore, Lyme disease is defined indirectly. Erythema migrans (EM) is the classic marker for this infection at early stages. However, not all patients infected with pathogenic *Borrelia* develop EM. In the absence of EM, the current basis for diagnosis is the demonstration of an antibody response against a pathogenic *Borrelia* in an appropriate clinical setting.

Unfortunately, current serologic assays for such antibodies suffer from both low sensitivity and specificity, especially in early disease. The U.S. Centers for Disease Control and Prevention (CDC) currently recommends that in order for a patient to be considered seropositive, two assays must be positive: a first tier assay, such as an ELISA, IFA or lateral flow assay, followed by a second tier assay, such as a western blot. This approach is expensive and can delay diagnosis for a week or more, but it is necessary because of the poor specificity of the most commonly used first tier assays. There is a need for a simple, sensitive and specific diagnostic method for the detection of Lyme disease, e.g. at early times after infection.

DESCRIPTION OF THE DRAWINGS

FIG. 2 shows sequence alignment of DbpB(38-67) in different strains of *Borrelia*. Sequences of full length DbpB from the indicated strains of *Borrelia* were aligned using the NCBI protein blast algorithm. Only the regions comprising DbpB(38-67), identified by epitope mapping, is displayed. The consensus sequence generated by the alignment is shown on the last line.

DESCRIPTION

Figure 1A:
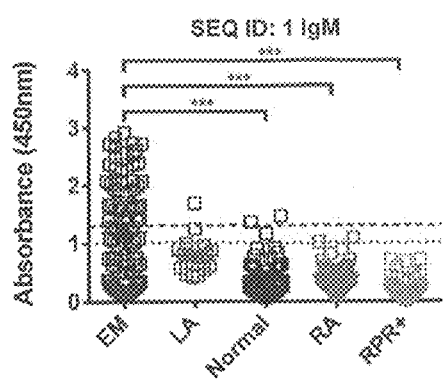
FIG. 1a shows representative data demonstrating enhanced binding of serum IgM to peptide SEQ ID: 1 in serum from patients with early Lyme disease (EM, erythema migrans) (n=103), late Lyme disease (LA, Lyme arthritis) (n=20), healthy controls (normal) (n=64), rheumatoid arthritis (RA) (n=46), or Syphilis (RPR+) (n=32). The dashed line represents the cutoff for positive binding, 3SD from the mean of healthy controls. The dotted line represents the cutoff for equivocal binding, 2SD from the mean of healthy controls. *p<0.05, ***p<0.001. Patient serum was added at a 1:100 dilution. Data were generated using standard ELISA techniques and a goat anti-human IgM (upper panel) or goat anti-human IgG (lower panel) secondary antibody to detect serum antibody binding.
Figure 1B:
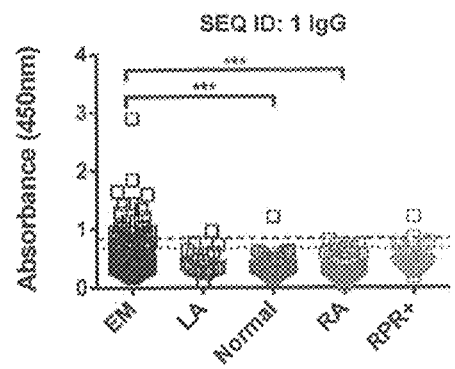
FIG. 1b shows representative data demonstrating enhanced binding of serum IgG to peptide SEQ ID: 1 in serum from patients with early Lyme disease (EM, erythema migrans) (n=103), late Lyme disease (LA, Lyme arthritis) (n=20), healthy controls (normal) (n=64), rheumatoid arthritis (RA) (n=46), or Syphilis (RPR+) (n=32). The dashed line represents the cutoff for positive binding, 3SD from the mean of healthy controls. The dotted line represents the cutoff for equivocal binding, 2SD from the mean of healthy controls. *p<0.05, ***p<0.001. Patient serum was added at a 1:100 dilution. Data were generated using standard ELISA techniques and a goat anti-human IgM (upper panel) or goat anti-human IgG (lower panel) secondary antibody to detect serum antibody binding.
Figure 1C:
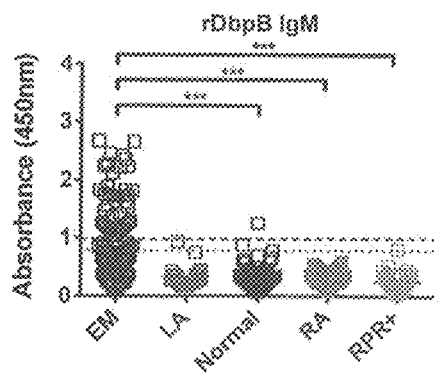
FIG. 1c shows representative data demonstrating enhanced binding of serum IgM to rDbpB protein in serum from patients with early Lyme disease (EM, erythema migrans) (n=103), late Lyme disease (LA, Lyme arthritis) (n=20), healthy controls (normal) (n=64), rheumatoid arthritis (RA) (n=46), or Syphilis (RPR+) (n=32). The dashed line represents the cutoff for positive binding, 3SD from the mean of healthy controls. The dotted line represents the cutoff for equivocal binding, 2SD from the mean of healthy controls. *p<0.05, ***p<0.001. Patient scrum was added at a 1:100 dilution. Data were generated using standard ELISA techniques and a goat anti-human IgM (upper panel) or goat anti-human IgG (lower panel) secondary antibody to detect scrum antibody binding.
Figure 1D:
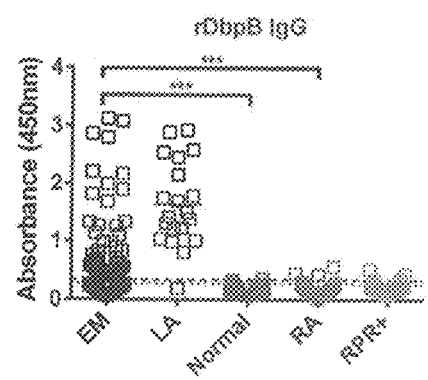
FIG. 1d shows representative data demonstrating enhanced binding of serum IgG to rDbpB protein in serum from patients with early Lyme disease (EM, erythema migrans) (n=103), late Lyme disease (LA, Lyme arthritis) (n=20), healthy controls (normal) (n=64), rheumatoid arthritis (RA) (n=46), or Syphilis (RPR+) (n=32). The dashed line represents the cutoff for positive binding, 3SD from the mean of healthy controls. The dotted line represents the cutoff for equivocal binding, 2SD from the mean of healthy controls. *p<0.05, ***p<0.001. Patient serum was added at a 1:100 dilution. Data were generated using standard ELISA techniques and a goat anti-human IgM (upper panel) or goat anti-human IgG (lower panel) secondary antibody to detect serum antibody binding.

The present inventors, by using a finely detailed epitope mapping strategy, have identified at least 3 peptides that can specifically and efficiently recognize antibodies to a pathogenic Borrelia which develop in a subject infected with a pathogen from the Borrelia burgdorferi sensu lato group. The peptides identified by the inventors were derived from the North American and European pathogenic species of B. burgdorferi, B. burgdorferi sensu lato (B. burgdorferi, B. garinii, and B. Afzelli). Some of the peptides which are discussed in the present application are represented by SEQ ID NOs: 1-3, as shown in Table 1.

TABLE 1

| Protein name/<br>position in<br>the protein | Sequence |
|---|---|
| B. burgdorferi<br>DbpB (38-67) | KDLKNKILKIKKEAT<br>GKGVLFEAFTGLKTG<br>(SEQ ID NO: 1) |
| B. garinii<br>DbpB (38-67) | DNVKNKILQIKEEAA<br>KKGVNFKAFTGTATG<br>(SEQ ID NO: 2) |
| B. afzelii<br>DbpB (38-67) | KDVKNKILQIKKDAE<br>DKGVNFAAFTSSETG<br>(SEQ ID NO: 3) |

The numbering of the amino acid residues of the peptides corresponds to the numbering of the amino acids in the corresponding full-length proteins.

One aspect of the invention is a composition comprising one or more of the isolated peptide KDLKNKILKIKKEATGKGVLFEAFTGLKTG (SEQ ID:1), or an active variant thereof in which one or more of the amino acids of SEQ ID NO:1 is substituted with an amino acid replacement, wherein the peptide or active variant can bind specifically to an antibody against a pathogenic Borrelia. In one aspect of the invention, the composition comprises the peptide of SEQ ID NO:1, but not the active variants. In one aspect of the invention, the active variants are represented by SEQ ID NO:2, SEQ ID NO:3 or SEQ ID NO:4. (KDLKNKILKIKKDATGKGVLFEAFTGLKTG).

One aspect of the invention is a composition comprising one or more of (SEQ ID NO: 1)
KDLKNKILKIKKEATGKGVLFEAFTGLKTG
and/or (SEQ ID NO: 2)
DNVKNKILQIKEEAAKKGVNFKAFTGTATG
and/or (SEQ ID NO: 3)
KDVKNKILQIKKDAEDKGVNFAAFTSSETG, or active variants thereof.

Any of the peptides of the invention can further comprise an N-terminal cysteine residue; and/or it can further comprise 1-3 additional and/or 1-3 fewer amino acids at one or both ends of the peptide.

One or more of the peptides in a composition of the invention may be linked to at least one further moiety, via a terminal amino acid linker or a chemical coupling agent. The at least one further moiety may be, e.g., an additional peptide that is specific for antibodies against the same or a different protein of the same or a different pathogenic Borrelia. In embodiments of the invention, the at least one further moiety is a second peptide that specifically recognizes an antibody against a pathogenic Borrelia, wherein the peptide and the second peptide are covalently linked, optionally via a spacer, and/or the at least one further moiety is a third peptide that specifically recognizes an antibody against a pathogenic Borrelia, wherein the peptide and/or the second peptide and/or the third peptide are covalently linked, optionally via a spacer.

Any of a variety of combinations of peptides may be linked in a multimeric peptide. Some representative multimeric peptides comprise, e.g., (SEQ ID NO: 6)
KDLKNKILKIKKEATGKGVLFEAFTG
LKTGGGGMKKNDQIVAAIALRGVA (SEQ ID NO: 7)
KDLKNKILKIKKEATGKGVLFEAFTG
LKTGGGGPFILEAKVRATTVAE (SEQ ID NO: 8)
KDLKNKILKIKKEATGKGVLFEAFTGLKTGGGGN
KTFNNLLKLTILVNGGGTILVNLLISCGLTGA (SEQ ID NO: 9)
KDLKNKILKIKKEATGKGVLFEAF
TGLKTGGGGNKTFNNLLKLTILVN (SEQ ID NO: 10)
DNVKNKILQIKEEAAKKGVNFKAFT
GTATGGGGMKKNDQIVAAIALRGVA (SEQ ID NO: 11)
DNVKNKILQIKEEAAKKGVNFKAF
TGTATGGGGPFILEAKVRATTVAE -continued

```
                              (SEQ ID NO: 12)
DNVKNKILQIKEEAAKKGVNFKAFTGTATGGGG

NKTFNNLLKLTILVNGGGTILVNLLISCGLTGA (SEQ ID NO: 13)
KDVKNKILQIKKDAEDKGVNFAAFT

SSETGGGMKKNDQIVAAIALRGVA (SEQ ID NO: 14)
KDVKNKILQIKKDAEDKGVNFAAF

TSSETGGGGPFILEAKVRATTVAE (SEQ ID NO: 15)
KDVKNKILQIKKDAEDKGVNFAAFTSSETGGGN

KTFNNLLKLTILVNGGGTILVNLLISCGLTGA
```

Another aspect of the invention is a diagnostic reagent comprising one or more of the isolated peptides, isolated compounds, or compositions described herein, and, optionally, a system for detecting the peptide(s) and/or a substrate for immobilizing the peptide(s).

Another aspect of the invention is a kit for diagnosing Lyme borreliosis, comprising one or more isolated peptides, isolated compounds, or compositions of the invention, and, optionally, a system for detecting the peptide(s) bound to an antibody to a pathogenic *Borrelia* protein and/or a substrate (e.g. a surface in a well or a bead, such as a polystyrene bead, for immobilizing the peptide(s). The peptides in a kit of the invention may be distributed in one or more containers.

Another aspect of the invention is a method for diagnosing Lyme disease in a subject, comprising contacting a sample from a subject suspected of having antibodies against a causative agent of Lyme disease with an isolated peptide, isolated compound, or composition of the invention, under conditions effective for the formation of a peptide-antibody complex, and detecting the presence of the peptide-antibody complex. In embodiments of the invention, the peptide-antibody complex is detected by adding a binding partner which is labeled, or which can be labeled with a signal generating reagent. The binding partner can be, e.g., an antibody attached to an enzyme, and a signal is generated when the enzyme reacts with a suitable substrate. In another embodiment, the detecting is performed with an ELISA assay. In another embodiment, the detecting is performed with a Luminex bead based assay; by microarray analysis, or lateral flow methods. The subject may be a mammal, such as, e.g., a cat, a dog, or a human.

Peptides of the invention bind specifically to an antibody induced by a causative agent of Lyme disease (a pathogenic *Borrelia*), e.g. in a sample from a subject having Lyme disease. An antibody "induced by" a pathogenic *Borrelia* is sometimes referred to herein as an antibody "against" the pathogenic *Borrelia*.

Generally, a peptide of the invention is derived from any one of a number of immunodominant proteins of a pathogenic *Borrelia* species that causes Lyme disease.

An "active variant" of a peptide of the invention is a peptide in which one or more of the amino acids is substituted with an amino acid replacement, wherein the peptide or variant can bind specifically to an antibody against a pathogenic *Borrelia*. In one embodiment of the invention, one or more of certain amino acids is substituted with a conservative or non-conservative amino acid replacement.

Suitable conservative amino acid substitutions will be evident to a skilled worker. For example, conservative replacements are those that take place within a family of amino acids that are related in their side chains and chemical properties. These include, e.g., (1) acidic: aspartate, glutamate; (2) basic: lysine, arginine, histidine; (3) nonpolar: alanine, valine, leucine, isoleucine, proline, phenylalanine, methionine, tryptophan; (4) uncharged polar: glycine, asparagine, glutamine, cysteine, serine, threonine, tyrosine; (5) aliphatic: glycine, alanine, valine, leucine, isoleucine, serine, threonine, with serine and threonine optionally be grouped separately as aliphatic-hydroxyl; (6) aromatic: phenylalanine, tyrosine, tryptophan; (7) amide: asparagine, glutamine; and (9) sulfur-containing: cysteine and methionine (see, for example, Biochemistry, 2nd ed., Ed. by L. Stryer, W H Freeman and Co.: 1981). Whether a change in the amino acid sequence of a peptide results in an active variant can be readily determined by assessing the ability of the variant peptide to produce a response in e.g. an ELISA in a fashion similar to the wild-type peptide, or to competitively inhibit such a response. Peptides in which more than one replacement has been introduced can be readily tested in the same manner. Generally, between one and about four codon changes can be present in such a variant. In embodiments, one, two, three, or four such changes are present in a variant consisting of one or more of the peptides listed in Table 1. Muteins and analogs are included.

As illustrated in FIG. 2, the inventors have aligned and compared the sequences of the peptides indicated in Table 1 from a wide variety of individual subspecies or isolates of *Borrelia burgdorferi* sensu lato, which includes all of the pathogenic *Borellia* genospecies that can cause Lyme disease, including *B. burgdorferi* sensu stricto, B, *garinii*, and *B. afzelli* as well as a few other minor ones that can cause disease in limited geographical regions. Each genospecies of the bacteria has multiple strains. Thus, each BLAST alignment may have dozens of different variants among the different strains in each genospecies. Using such alignments, a skilled worker can readily determine which amino acid residues are conserved and may be important for the ability to bind specifically and efficiently to antibodies to pathogenic *Borrelia* which develop in a subject infected with a pathogen from *Borrelia*; and which amino acids differ between peptides from these strains, but the peptides appear to retain at least some of the binding specificity and efficacy, and thus these amino acids appear to be nonessential (or at least not very important) for this activity. Consensus sequences for each of the three principle pathogenic strains of *Borrelia* (*B. burgdorferi*, *B. garinii*, and *B. afzelii*) are depicted by SEQ ID:1, SEQ ID:2, and SEQ ID:3 respectively, derived in part on the basis of such alignments, and in part on confirmatory ELISA analysis as described elsewhere herein. The analysis also indicates active variants of the peptides; the active variants can bind specifically to an antibody against a pathogenic *Borrelia*. In the active variants, one or more of the indicated amino acids can be substituted with an amino acid replacement, such as a conservative amino acid replacement.

KDLKNKILKI KKEATGKGVL FEAFTGLKTG (DbpB 38-67), (SEQ ID: 1)

In active variants of this peptide, such as those described in SEQ ID: 2 and SEQ ID: 3, one or more amino acids K1, D2, L3, K9, K12, K13, T15, G16, L20, E22, G26, L27, and/or K28 can be substituted with an amino acid replacement.

The term "a peptide of the invention," as used herein, refers to a peptide represented by any of the sequences shown in Table 1, or an active variant thereof, particularly those peptides which contribute to specific and sensitive assays. A "composition of the invention," as used herein, refers to a composition which comprises one of more of the peptides discussed herein.

Based on sequence comparisons such as the ones described above, a skilled worker can generate consensus sequences that represent SEQ ID NO:1 and active variants thereof. For example, SEQ ID NO: 1 can be represented by the consensus sequence (K or D) (D or N) (L or V) K N K I L (K or Q) I K (K or E) (K or D) A (T or A or E) (G or E or K or D) K G V (L or N) F (E or K) A F T (G or S) (L or S or T) (K or A or E) T G (SEQ ID NO:16). Other amino acids (either homologous or non-homologous) can also be substituted at the variable positions, provided the substitutions do not significantly impact the ability of the peptide to bind to an antibody generated against infection with a pathogenic Borrelia.

Any of the peptides of the invention can optionally contain a cysteine (C) residue at its N terminus, e.g. to facilitate the attachment of a biotin molecule, which can be useful for binding the peptide to a surface comprising avidin.

A peptide, including a modified form thereof, which "binds specifically" to ("is specific for"; binds "preferentially" to) an antibody against a pathogenic Borrelia interacts with the antibody, or forms or undergoes a physical association with it, in an amount and for a sufficient time to allow detection of the antibody. By "specifically" or "preferentially" is meant that the peptide has a higher affinity, e.g. a higher degree of selectivity, for such an antibody than for other antibodies in a sample. That is, the peptide has an affinity for the antibody of at least about 2-fold higher than for other antibodies in the sample. The affinity or degree of specificity can be determined by a variety of routine procedures, including, e.g., competitive binding studies.

An "isolated" peptide of the invention is in a form other than it occurs in nature, e.g. in a buffer, in a dry form awaiting reconstitution, as part of a kit, etc. In some embodiments, the peptide is substantially purified. The term "substantially purified", as used herein refers to a molecule, such as a peptide, that is substantially free of other proteins, lipids, carbohydrates, nucleic acids and other biological materials with which it is naturally associated. For example, a substantially pure molecule, such as a peptide, can be at least about 60%, by dry weight, preferably at least about 70%, 80%, 90%, 95%, or 99% the molecule of interest. An isolated or purified peptide of the invention differs from the protein from which it was derived at least because of broken bonds between the ends of the peptide and the intact protein. Synthetic peptides are, of course, not naturally occurring.

The peptides of the invention may be modified by a variety of techniques, such as by denaturation with heat and/or SDS. A peptide of the invention may be modified to provide an additional N- or C-terminal amino acid sequence suitable for biotinylation, e.g., cysteine or lysine; suitable for chemical lipidation, e.g., cysteine; or the like.

Peptides of the invention may be modified by any of a variety of known modifications. These include, but are not limited to, glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in many basic texts, such as Proteins—Structure and Molecular Properties, 2nd ed., T. E. Creighton, W.H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (1990) Meth. Enzymol. 182:626-646 and Rattan et al. (1992) Ann. N.Y. Acad. Sci. 663:48-62.

Peptides of the invention that consist of any of the sequences discussed herein may be modified by any of the discussed modifications. Such peptides still "consist of" the amino acids.

Peptides of the invention may be associated with one or more further moieties. The association can be covalent or non-covalent, and can be, for example, via a terminal amino acid linker (such as Lys or Cys) or a chemical coupling agent. An additional moiety can be, e.g., a detectable label, a fusion partner (such as a chemical compound or a peptide having an epitope of another pathogenic Borrelia), or a substrate that immobilizes the peptide (e.g. a microwell plate, an Immobilon or nitrocellulose membrane, or latex or polystyrene beads).

A peptide of the invention can be fused to a fusion partner (e.g. a peptide or other moiety) that can be used to improve purification, to enhance expression of the peptide in a host cell, to aid in detection, to stabilize the peptide, etc. Examples of suitable compounds for fusion partners include polyethylene glycol, PEGylation, or other chemicals. Among the many suitable peptide or polypeptide fusion partners are, e.g., β-galactosidase, glutathione-S-transferase, a histidine tag, etc. In some embodiments, a peptide of the invention is provided with a detectable label, such as those described below.

A peptide of the invention can be associated with a substrate that immobilizes the peptide. The substrate can be, e.g., a solid or semi-solid carrier, support or surface, including a bead. The association can be covalent or non-covalent, and can be facilitated by a moiety associated with the peptide that enables covalent or non-covalent binding, such as a moiety that has a high affinity to a component attached to the carrier, support or surface. For example, the peptide can be associated with a biotin moiety, and the component associated with the surface can be avidin. The peptide can be immobilized on the solid or semi-solid surface or carrier either prior to or after the addition of the sample containing antibody.

A peptide of the invention may be used in combination with one or more additional peptides or polypeptides from the same or a different protein, from the same or a different pathogenic Borrelia strain, wherein the additional peptide(s) or polypeptide(s) also bind specifically to an antibody against a pathogenic Borrelia. The combination may comprise a cocktail (a simple mixture) of individual peptides or polypeptides, or it may be in the form of a fusion peptide or polypeptide (a multimeric peptide). For example, a peptide of the invention may be fused at its N-terminus or C-terminus to another suitable peptide. Two or more copies of a peptide of the invention may be joined to one another, alone or in combination with one more additional peptides. Combinations of fused and unfused peptides or polypeptides can be used. In one embodiment, the additional peptide(s) contain B-cell and/or T-cell epitopes from a protein of a pathogenic *Borrelia*.

Any combination of two or more peptides of the invention can be combined to form a multimeric (multi-epitope) peptide. Furthermore, the peptides can be combined with suitable additional peptides or polypeptides (sometimes referred to herein as "antigenic peptides or polypeptides" or as "agents") that can be derived from *Borrelia* antigens such as OspA, OspB, DbpA, flagella-associated proteins FlaA (p37) and FlaB(p41), OspC (25kd), BBK32, BmpA(p39), p21, p39, p66 or p83. See, e.g., Barbour et al (1984) *Infect. Immun.* 45, 94-100; Simpson et al. (1990) *J. Clin. Microbiol.* 28, 1329-1337; Hansen et al. (1988) *Infect. Immun.* 56, 2047-2053; Hansen et al. (1988) *Infect. J. Clin. Microbiol.* 26, 338-346; Wilske et al. (1986) *Zentral, Bakteriol, Parsitenkd, Infektionshkr, Hyg. Abt.* 1 *Orig. Reihe, A.* 263, 92-102; Dorward et al. (1991) *J. Clin. Microbiol.* 29, 1162-1170; published NTIS U.S. patent application No. 485,551; European patent application No. 465,204; International Patent Application No. PCT/US91/01500; International Patent Application No. PCT/EP90/02282; International Patent Application No. PCT/DK89/00248; International patent application No. WO92/00055. The peptides described in U.S. Pat. No. 7,887,815 can also be used, as can the 26 amino acid peptide derived from the IR6 region of the *B. burgdorferi* VlsE, which is currently approved by the FDA for use in a peptide-based immunodiagnostic assay in the United States. Polypeptides or peptides derived from other microorganisms can also be used.

One aspect of the invention is an isolated compound comprising an isolated peptide as discussed above, linked to at least one further moiety, via a terminal amino acid linker or a chemical coupling agent. The further moiety can be, e.g., a second peptide that specifically recognizes an antibody against a pathogenic *Borrelia*, wherein the peptide and the second peptide are covalently linked. In embodiments of the invention, the peptide and the second peptide are separated from one another by a spacer of 1-5 Glycine or Alanine residues. Any of these isolated compounds can be included in a composition of the invention.

A composition of the invention can further comprise, in additional to the individual peptides discussed herein, one or more additional peptides which are diagnostic of Lyme disease (are specific for antibodies against the same or different proteins of the same or a different pathogenic *Borrelia*). Any of the peptides discussed herein can be combined, in any order and in any number of copies, to form a multimeric (multi-epitope) peptide. Some representative examples of combinations of peptides of the invention, with typical amino acid linker moieties, are described herein. However, it will be evident to a skilled worker that any of a variety of these or other combinations can be used. For example, one aspect of the invention is a composition comprising, in addition to or instead of the peptides in the compositions discussed above, one or more of the diagnostic peptides disclosed in PCT International Patent Application No. PCT/US2013/024370 and/or in PCT International Application No. PCT/US2010/034885, both of which are incorporated by reference herein in their entireties, particularly with reference to the diagnostic peptides, or active variants thereof, in which one or more of the amino acids is substituted with an amino acid replacement, wherein the peptide or variant can bind specifically to an antibody against a pathogenic *Borrelia*: In other embodiments, the additional peptide comprises an epitope from *Borrelia* flagellin p41 (e.g., the peptide having the sequence VQEGVQQEGAQQP (SEQ ID NO:17)), and/or an epitope from *Borrelia* OspC (e.g., the peptide having the sequence PVVAESPKKP (SEQ ID NO:18)). Alternatively, or in addition, a composition of the invention can further comprise a peptide from the VLsE (region IR6) *Borrelia* protein (e.g. the 26 amino acid peptide CMKKDDQIAAA MVLRG-MAKDGQFALK (SEQ ID NO:19), which is currently in commercial use), or a shorter, 17 amino acid peptide from this region, MKKNDQI(V or G)AAIALRGVA (SEQ ID NO:20), or active variants thereof. The 17 amino acid peptide and active variants thereof are described in detail in U.S. Pat. No. 7,887,815, which is incorporated by reference herein.

One aspect of the invention is a peptide of the invention that is linked to (e.g. associated with, coupled, or fused to, directly or indirectly) one or more additional moieties. The association may be, for example, via a terminal amino acid linker (such as Lys or Cys) or a chemical coupling agent. A peptide may be linked directly to one or more moieties, such as other peptides. For example, a peptide may be synthesized so as to contain a peptide of the invention flanked by one or more additional peptides (e.g. from *Borrelia*), on its N-terminus, its C-terminus, or both. In one embodiment, linked peptides are separated by a spacer. The spacer may consist, for example, of between about one and five (e.g., three) amino acids, preferably uncharged amino acids, e.g., aliphatic amino acids such as Gly or Ala. In one embodiment, the spacer is a triple Gly spacer. A linker may, e.g., provide distance between epitopes of different antigenic peptides. The additional moiety can be, e.g., a detectable label, a fusion partner (such as a chemical compound, or a peptide having an epitope from the same or a different protein from the same or a different pathogenic *Borrelia*), or a substrate that immobilizes the peptide (e.g. a microwell plate, an Immobilon or nitrocellulose membrane, or latex beads).

One aspect of the invention is a composition comprising a peptide of the invention and, optionally, one or more additional polypeptides or peptides that specifically recognize antibodies to a causative agent of Lyme disease. Any combination of 1, 2, 3, 4, 5, 5, 7, 8, 9, 10, 11, 12, 13, 14, 15 or more of the peptides of the invention, including active variants of the peptides listed in Table 1 or FIG. 2, can be present in such a combination; or other suitable peptides can be used. The additional polypeptides or peptide(s) may be used in conjunction with a peptide of the invention as part of a cocktail; or one or more of the additional polypeptides or peptides may be fused at the N-terminus and/or the C-terminus of a peptide of the invention to form a fusion peptide or polypeptide. The terms peptide and polypeptide are used interchangeably herein; for example, an amino acid consisting of three 9-15-mer peptides linked directly to one another can be referred to as either a peptide or a polypeptide.

An isolated peptide of the invention (including multi-epitope peptides) can be of any desirable size. For example, it can consist of 1, 2, or 3 or more, or 1, 2, or 3 fewer, amino acids from the N-terminus, the C-terminus, or both termini of a peptide of the invention. In general, because peptides smaller than 8 amino acids are not functional for binding to an antibody, peptides of the invention are generally no smaller than 8 amino acids. In embodiments of the invention, a peptide is no more than 18, 20, 22, 24, 26, 28, 30, 35, 40, 45, 50, 55 or 60 amino acids in length. Peptides which are too long, such a full-length proteins, generally engage in non-specific interactions and thus are not specific enough to be suitable for an assay of the present invention.

Other suitable peptides include any of the other peptides described herein which further comprise, attached at the N-terminal and/or C-terminal end, one or more of the consecutive amino acids from the *B. burgdorferi* strain from which the peptide was isolated, which abut the peptide sequences in the naturally occurring protein from which the peptide is derived, or active variants of those sequences. Optionally, such a peptide can contain an N-terminal Cys or Lys residue, e.g. to facilitate the addition of a Biotin molecule. Furthermore, active variants of the peptides are included. An isolated peptide of the invention can be associated with a second moiety, used as a diagnostic reagent, present in a composition comprising one or more additional polypeptides or peptides that specifically recognize antibodies to a causative agent of Lyme disease, or present in a kit for diagnosing Lyme disease.

One embodiment of the invention—a composition comprising a peptide of the invention and one or more additional agent(s)—is particularly well-suited for diagnosing *Borrelia* infections early after infection (e.g., within one to two weeks after the onset of infection). Among the pathogenic *Borrelia* proteins whose expression has been recognized in early human infection (e.g. to which IgM antibody appears early after infection) are OspC, BBK32, the flagella-associated protein, FlaB(p41), and, to a lesser extent, BmpA(p39), VlsE and the flagella-associated protein, FlaA(p37). Polypeptides or peptides which derive from those polypeptides are suitable for assays for early infection. It is expected that any of the peptides described herein will be useful for early detection.

Some suitable linear epitopes which can be used for the diagnosis of early infection include peptides identified in OspC: PVVAESPKKP (SEQ ID NO: 18), reported by Steere et al. (1987) *Ann. Intern Med.* 107, 725-731; ILMTLFLFIS-CNNS (SEQ ID NO:21), reported by AC Steere (2001) *N Engl J Med* 345, 115-25; and one or more epitopes contained between amino acids 161 and 210, reported by Jobe et al. (2003) *Clin Diagn Lab Immunol* 10, 573-8)]. The OspC peptides described in U.S. Pat. No. 6,716,574 can also be used. Other suitable regions, which have been shown not contain major cross-reactive epitopes, have been identified in FlaB(p41), e.g. residues 120 to 235. See, e.g., Crother et al. ((2003) *Infect. Immun.* 71, 3419-3428 and Wang et al. (1999)) *Clin Microbial Rev* 12, 633-653. Other peptides bearing either linear or conformational epitopes are known in the art.

In one embodiment, a peptide from the IR6 region of *B. garinii*, (e.g. the 26 amino acid peptide CMKKDDQIAAA MVLRGMAKDGQFALK (SEQ ID NO:19), which is currently in commercial use, or a shorter, 17 amino acid peptide from this region, MKKDDQIAAAIALRGMA (SEQ ID NO:22). The 17 amino acid peptide and active variants thereof are described in detail in U.S. Ser. No. 12/292,044, which is incorporated by reference herein.

Variants of previously identified epitopes can be readily selected by one of skill in the art, based in part on known properties of the epitopes. For example, a known epitope may be lengthened or shortened, at one or both ends, by about 1-3 amino acids; one, two or more amino acids may be substituted by conservative amino acids; etc. Furthermore, if a region of a protein has been identified as containing a suitable epitope, an investigator can "shift" the region of interest (select different sub-sequences) up to about 5 amino acids in either direction from the endpoints of the original rough region, e.g. to optimize the activity. Methods for confirming that variant peptides are suitable are conventional and routine. Methods for identifying additional epitopes, particularly from variable regions rather than the conserved regions discussed above (e.g. from OspC, BBK32 or DbpA), are discussed in the Examples.

Polypeptides comprising linked peptides may be of any suitable length (e.g. between about 20-80 amino acids, or more), and they may contain any desirable number of linear epitopes (e.g. between about 2-5, or more). For example, between 3 to 5 peptides of about 9-15 amino acids each may be combined, optionally in the presence of suitable spacers, to generate a polypeptide of about 45-50 amino acids. A length of about 120 amino acids can be readily synthesized chemically by current technologies. Other methods may be used to generate longer peptides. The peptides can be linked in any order.

It is expected that multi-epitope peptides of the invention will exhibit significantly more binding to sera from subjects infected with *Borrelia burgdorferi* sensu lato than does one of the peptides of the invention, alone. Methods for making and testing typical multi-epitope peptides are shown elsewhere herein.

In one embodiment of the invention, a composition comprising one or more of the peptides of the invention and, optionally, one or more of the above-mentioned additional peptides (e.g. in the form of a cocktail or a fusion peptide or polypeptide) is used in a single tier assay, for detecting early/or and late stage Lyme disease. Such a peptide cocktail or fusion polypeptide can be effective in the diagnosis of Lyme disease as caused by a wide spectrum of pathogenic *Borrelia* isolates.

Fusion peptides or polypeptides (multimeric proteins) of the invention can be produced recombinantly or synthesized chemically. They may also include a peptide of the invention fused or coupled to moieties other than amino acids, including lipids and carbohydrates.

A peptide of the present invention can be in the form of a pharmaceutically acceptable salt. Suitable acids and bases that are capable of forming salts with the peptides of the present invention are well known to those of skill in the art, and include inorganic and organic acids and bases.

A peptide of the invention can be produced using conventional chemical synthesis techniques, such as those described, e.g., in G. Barony et al., The Peptides: Analysis, Synthesis & Biology, Academic Press, pp. 3-285 (1980). Such chemically synthesized peptides can be obtained from commercial suppliers. Peptides produced by chemical synthesis can be obtained at purities exceeding about 95%. Therefore, there is typically a much reduced likelihood for undesirable cross reactivity with random antibodies than by using peptides obtained by other methods.

Alternatively, a peptide of the invention can be produced recombinantly following conventional genetic engineering techniques. To produce a recombinant peptide of the invention, a nucleic acid encoding the peptide is inserted into a suitable expression system. Generally, a recombinant molecule or vector is constructed in which the polynucleotide sequence encoding the selected peptide is operably liked to an expression control sequence permitting expression of the peptide. Numerous types of appropriate expression vectors are known in the art, including, e.g., vectors containing bacterial, viral, yeast, fungal, insect or mammalian expression systems. Methods for obtaining and using such expression vectors are well-known. For guidance in this and other molecular biology techniques used for compositions or methods of the invention, see, e.g., Sambrook et al, Molecular Cloning, A Laboratory Manual, current edition, Cold Spring Harbor Laboratory, New York; Miller et al, Genetic Engineering, 8:277-298 (Plenum Press, current edition), Wu et al, *Methods in Gene Biotechnology* (CRC Press, New York, N.Y., current edition), *Recombinant Gene Expression Protocols, in Methods in Molecular Biology*, Vol. 62, (Tuan, ed., Humana Press, Totowa, N.J., current edition), and *Current Protocols in Molecular Biology*, (Ausabel et al, Eds.,), John Wiley & Sons, NY (current edition), and references cited therein.

Suitable host cells or cell lines for the recombinant nucleic acids or vectors of the invention transfection by this method include bacterial cells. For example, various strains of *E. coli* (e.g., HB 101, MC1061) are well-known as host cells in the field of biotechnology. Various strains of *B. subtilis, Pseudomonas, Streptomyces*, and other bacilli and the like can also be employed in this method. Alternatively, a peptide of the invention can be expressed in yeast, insect, mammalian, or other cell types, using conventional procedures.

Thus, the present invention provides a method for producing a recombinant peptide or polypeptide, which involves transfecting or transforming, e.g., by conventional means such as electroporation, a host cell with at least one expression vector containing a polynucleotide of the invention under the control of an expression control sequence (e.g. a transcriptional regulatory sequence). The transfected or transformed host cell is then cultured under conditions that allow expression of the peptide or polypeptide. The expressed peptide or polypeptide is recovered, isolated, and optionally purified from the cell (or from the culture medium, if expressed extracellularly) by appropriate means known to one of skill in the art, including liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention. One skilled in the art can determine the purity of the peptide or polypeptide by using standard methods including, e.g., polyacrylamide gel electrophoresis (e.g. SDS-PAGE); column chromatography (e.g. high performance liquid chromatography (HPLC)), or amino-terminal amino acid analysis.

Included in the invention are a polynucleotide encoding and/or expressing a peptide or polypeptide of the invention, a vector comprising the polynucleotide, and a host cell comprising the polynucleotide acid or vector.

One aspect of the invention is a method for detecting Lyme disease in a subject suspected of having antibody against a causative agent of Lyme disease. The diagnostic method is useful for diagnosing subjects exhibiting the clinical symptoms of, or suspected of having, Lyme disease.

The subject can be any subject (patient) in which antibodies can be made against the causative agent and detected. Typical subjects include vertebrates, such as mammals, including wildlife (e.g. mice and chipmunks), dogs, cats, non-human primates and humans.

In one embodiment, the diagnostic method involves detecting the presence of naturally occurring antibodies against pathogenic *Borrelia* (e.g. *B. Burgdorferi*) which are produced by the infected subject's immune system in its biological fluids or tissues, and which are capable of binding specifically to a peptide of the invention or combinations of a peptide of the invention and, optionally, one or more suitable additional antigenic polypeptides or peptides.

One aspect of the invention is a method for diagnosing Lyme disease in a subject (e.g. for diagnosing exposure to and/or infection by a pathogenic *Borrelia*), comprising measuring a bodily fluid (which would be expected to contain antibodies) of the subject for the presence of an antibody against a causative agent of Lyme disease (e.g. an antibody capable of binding to such an agent), wherein an elevated level of antibody in the subject compared to a corresponding level of antibody in a control (such as a known unaffected subject) indicates an infection by the causative agent and/or that the subject has Lyme disease. A "causative agent for Lyme disease," as used herein, includes a pathogenic species of *B. burgdorferi, B. afzelli*, or *B. garinii*. Screening with serum derived from both North America and Europe indicates that screening with peptides derived from *burgdorferi* are predictive of reactivity to the same peptide present in the other two strains. If this were not the case, the European Lyme serum would not bind to peptides the inventors used for these studies. Other species of *Borrelia* which have been implicated in Lyme disease, such as, e.g., *B. lusitaniae* and *B. valaisianae*, are also included, provided they induce antibodies which can react specifically with a peptide of the invention. It is to be understood that the term "pathogenic *Borrelia*," as used herein, refers to any such pathogenic genospecies that causes Lyme disease. "Lyme disease," as used herein, refers to an disease which exhibits the characteristics as summarized in Dattwyler, R. J. and Wormser, G. "Lyme borreliosis." in Infectious Diseases Medicine and Surgery (eds.) S. Gorbach and J. Bartlett, $3^{rd}$ edition, Saunders Pub. New York, N.Y., 2003 and which is caused by a pathogenic *Borrelia*.

One embodiment of this method comprises contacting (incubating, reacting) a peptide of the invention with a sample of a biological fluid (e.g. serum or CSF) from a subject (e.g. human or other animal) to be diagnosed (a subject suspected of having Lyme disease). In the presence of an antibody response to infection with a pathogenic *Borrelia*, an antigen-antibody complex is formed. The antigen-antibody complex is sometimes referred to herein as an antibody-peptide complex, a peptide-antibody complex, or an antibody-epitope complex; these terms are used interchangeably. Subsequently the reaction mixture is analyzed to determine the presence or absence of this antigen-antibody complex. A variety of conventional assay formats can be employed for the detection, such, e.g., as ELISA, microarray analysis, Luminex bead based assays or lateral flow methods. The presence of an elevated amount of the antibody-peptide complex indicates that the subject was exposed to and infected with a pathogenic *Borrelia* capable of causing Lyme disease. In any detection assay of the invention, a positive response is defined as a value 2 or 3 standard deviations greater than the mean value of a group of healthy controls. For the purposes of the initial screening, the inventors defined a positive response to the peptide as a statistically significant difference in the mean binding of serum antibodies from patients with confirmed Lyme disease, compared to serum from patients confirmed to be sero-negative for Lyme disease (normal controls), and serum from patients that are positive for Syphilis (RPR+), where significance is measured as $p<0.05$ as determined using a Kruskal-Wallis test followed by a Dunn's comparison test. Serum antibody binding was compared at single dilutions (1:50), as well as reciprocal 50% binding titers (several dilutions of each serum sample were prepared and incubated with each peptide; the 50% binding titer was determined as the dilution of antibody at which the absorbance measured in the ELISA assay had reached 50% of the maximum absorbance recorded for any of the dilutions). Ultimately, when a multi-peptide assay has been completed, the cutoff for a positive response will be greater than 3 SD from the mean of a group of healthy controls. In some embodiments, a second tier assay is required to provide an unequivocal sero-diagnosis of Lyme disease.

One embodiment of the invention is a diagnostic immunoassay method, which comprises (1) taking a sample of body fluid or tissue likely to contain antibodies; (2) contacting the sample with a peptide of the invention, under conditions effective for the formation of a specific peptide-antibody complex (for specific binding of the peptide to the antibody), e.g., reacting or incubating the sample and a peptide; and (3) assaying the contacted (reacted) sample for the presence of an antibody-peptide reaction (e.g., determining the amount of an antibody-peptide complex).

As used herein, the singular forms "a," "an," and "the" include plural referents unless the context clearly dictates otherwise. Thus, "a" peptide of the present invention, as used above, can be two or more peptides, which can be the same or different. Similarly, when an isolated peptide of the invention is in association with (e.g., linked to) "an" additional peptide, the isolated peptide can be associated with one or more additional peptides.

Phrases such as "sample containing an antibody" or "detecting an antibody in a sample" are not meant to exclude samples or determinations (detection attempts) where no antibody is contained or detected. In a general sense, this invention involves assays to determine whether an antibody produced in response to infection with a pathogenic *Borrelia* is present in a sample, irrespective of whether or not it is detected.

Conditions for reacting peptides and antibodies so that they react specifically are well-known to those of skill in the art. See, e.g., Current Protocols in Immunology (Coligan et al., editors, John Wiley & Sons, Inc) or the Examples herein.

A diagnostic method of the invention can comprise taking a sample of body fluid or tissue likely to contain antibodies. The antibodies can be, e.g., of IgG, IgE, IgD, IgM, or IgA type. Generally, IgM and/or IgA antibodies are detected, e.g. for the detection of early infection. IgG antibodies can be detected when some of the additional peptides discussed above are used in the method (e.g. peptides for the detection of flagellum proteins). The sample is preferably easy to obtain and may be serum or plasma derived from a venous blood sample or even from a finger prick. Tissue from other body parts or other bodily fluids, such as cerebro-spinal fluid (CSF), saliva, gastric secretions, mucus, etc. are known to contain antibodies and may be used as a source of the sample.

Once the peptide antigen and sample antibody are permitted to react in a suitable medium, an assay is performed to determine the presence or absence of an antibody-peptide reaction. Among the many types of suitable assays, which will be evident to a skilled worker, are immunoprecipitation and agglutination assays.

In embodiments of the invention, the assay may comprise (1) immobilizing the antibody(s) in the sample, adding a peptide of the invention, and then detecting the degree of antibody bound to the peptide, e.g. by the peptide being labeled or by adding a labeled substance (conjugate, binding partner), such as a labeled antibody, which specifically recognizes the peptide; (2) immobilizing a peptide of the invention, adding the sample containing an antibody(s), and then detecting the amount of antibody bound to the peptide, e.g. by adding a labeled substance (conjugate, binding partner), such as a labeled antibody, which specifically recognizes the antibody; or (3) reacting the peptide and the sample containing antibody(s) without any of the reactants being immobilized, and then detecting the amount of complexes of antibody and peptide, e.g. by the peptide being labeled or by adding a labeled substance (conjugate, binding partner), such as a labeled antibody, which specifically recognizes the peptide.

Immobilization of a peptide of the invention can be either covalent or non-covalent, and the non-covalent immobilization can be non-specific (e.g. non-specific binding to a polystyrene surface in e.g. a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin or an analogue thereof. An alternative is a situation in which the moiety has the amino acid sequence His-His-His-His-His-His (SEQ ID NO:23) and the carrier comprises a Nitrilotriacetic Acid derivative (NTA) charged with $Ni^{++}$ ions. Among suitable carriers, supports or surface are, e.g., magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (supra). In a preferred assay, a peptide of the invention is immobilized to the solid or semi-solid surface or carrier by means of covalent or non-covalent binding, either prior to or after the addition of the sample containing antibody.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices, dipsticks and immunocapillary or immunochromatographic immunoassay devices.

In embodiments of the invention, the solid or semi-solid surface or carrier is the floor or wall in a microtiter well; a filter surface or membrane (e.g. a nitrocellulose membrane or a PVDF (polyvinylidene fluoride) membrane, such as an Immobilon membrane); a hollow fiber; a beaded chromatographic medium (e.g. an agarose or polyacrylamide gel); a magnetic bead; a fibrous cellulose matrix; an HPLC matrix; an FPLC matrix; a substance having molecules of such a size that the molecules with the peptide bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

In one embodiment of the invention, peptides of the invention are immobilized onto tiny polystyrene beads (microspheres), wherein each peptide is immobilized onto a bead with a unique spectral signature, and are analyzed by the xMAP® technology developed by Luminex Technology (Austin, Tex.) and described in their world wide web site luminexcorp.com.

In some embodiments of the invention, the peptide is provided with a suitable label which enables detection. Conventional labels may be used which are capable, alone or in concert with other compositions or compounds, of providing a detectable signal. Suitable detection methods include, e.g., detection of an agent which is tagged, directly or indirectly, with a fluorescent label by immunofluorescence microscopy, including confocal microscopy, or by flow cytometry (FACscan); detection of a radioactively labeled agent by autoradiography; electron microscopy; immunostaining; subcellular fractionation, or the like. In one embodiment, a radioactive element (e.g. a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody which binds to the first antibody. This secondary antibody can be labeled, e.g., with a radioactive, enzymatic, fluorescent, luminescent, or other detectable label, such as an avidin/biotin system.

A "detection system" for detecting bound peptide, as used herein, may comprise a detectable binding partner, such as an antibody specific for the peptide. In one embodiment, the binding partner is labeled directly. In another embodiment, the binding partner is attached to a signal generating reagent, such as an enzyme that, in the presence of a suitable substrate, can produce a detectable signal. A surface for immobilizing the peptide may optionally accompany the detection system.

In embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

In one embodiment of the method, the peptide, or a mixture of peptides, is electro- or dot-blotted onto nitrocellulose paper. Subsequently, the biological fluid (e.g. serum or plasma) is incubated with the blotted antigen, and antibody in the biological fluid is allowed to bind to the antigen(s). The bound antibody can then be detected, e.g. by standard immunoenzymatic methods.

In another embodiment of the method, latex or polystyrene beads are conjugated to the antigen(s) of the invention. Subsequently, the biological fluid is incubated with the bead/peptide conjugate, thereby forming a reaction mixture. The reaction mixture is then analyzed to determine the presence of the antibodies.

One assay for the screening of blood products or other physiological or biological fluids is an enzyme linked immunosorbant assay, i.e., an ELISA. Typically in an ELISA, the isolated antigen(s) of the invention is adsorbed to the surface of a microtiter well directly or through a capture matrix (i.e., antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-pathogenic Borrelia (e.g. B. burgdoferi) antibody. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin ($\alpha$HuIg) from another animal, such as dog, mouse, cow, etc.) that is conjugated to an enzyme or other label by standard procedures and is dissolved in blocking buffer. The label can be chosen from a variety of enzymes, including horseradish peroxidase (HRP), $\beta$-galactosidase, alkaline phosphatase, glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD+3 standard deviations (SDs) of at least 50 serum samples collected from individuals from an area where Lyme disease is not endemic, or by other such conventional definitions. In the case of a very specific assay, OD+2 SD can be used as a cutoff value.

In one embodiment of an ELISA, a peptide of the invention is immobilized on a surface, such as a ninety-six-well ELISA plate or equivalent solid phase that is coated with streptavidin or an equivalent biotin-binding compound at an optimal concentration in an alkaline coating buffer and incubated at 4° C. overnight. After a suitable number of washes with standard washing buffers, an optimal concentration of a biotinylated form of a composition/antigen of this invention dissolved in a conventional blocking buffer is applied to each well; a sample is added; and the assay proceeds as above.

Another useful assay format is a lateral flow format. Antibody to human or animal antibody or staph A or G protein antibodies is labeled with a signal generator or reporter (i.e. colloidal gold) that is dried and placed on a glass fiber pad (sample application pad). The diagnostic peptide is immobilized on membrane, such as a PVDF (polyvinylidene fluoride) membrane (e.g. an Immobilon membrane (Millipore)) or a nitrocellulose membrane. When a solution of sample (blood, serum, etc) is applied to the sample application pad, it dissolves the colloidal gold labeled reporter and this binds to all antibodies in the sample. This mixture is transported into the next membrane (PVDF or nitrocellulose containing the diagnostic peptide) by capillary action. If antibodies against the diagnostic peptide are present, they bind to the diagnostic peptide striped on the membrane generating a signal. An additional antibody specific to the colloidal gold labeled antibody (such as goat anti-mouse IgG) is used to produce a control signal.

It should be understood by one of skill in the art that any number of conventional protein assay formats, particularly immunoassay formats, may be designed to utilize the isolated peptides of this invention for the detection of pathogenic Borelia (e.g. B. burgdorferi) infection a subject. This invention is thus not limited by the selection of the particular assay format, and is believed to encompass assay formats that are known to those of skill in the art.

Reagents for ELISA or other assays according to this invention can be provided in the form of kits. Such kits are useful for diagnosing infection with a pathogenic *Borrelia* (e.g. a *B. burgdorferi*), using a sample from a subject (e.g. a human or other animal). Such a diagnostic kit can contain an peptide of the invention (and, if desired, additional peptides as discussed above) and, optionally, a system for (means enabling) detection of a peptide of the invention bound to an antibody against a protein from a pathogenic *Borrelia*, and/or a surface to which the peptide can be bound. In one embodiment, a kit contains a mixture of suitable peptides or means for preparing such mixtures, and/or reagents for detecting peptide-antibody complexes.

Another aspect of the invention is a kit for diagnosing Lyme disease in a subject, which comprises one or more peptides of the invention, or one or more compositions of the invention, and optionally comprises one or more additional peptides or polypeptides as noted above. The peptide(s) may comprise a detectable label, or the kit may include a detection system (e.g. a labeled conjugate and a reagent; or beads comprising unique spectral signatures) for detecting a peptide which is specifically bound to an antibody in the sample. In one embodiment, the kit contains a substrate for immobilizing the peptide, such as a microwell plate, an Immobilon or nitrocellulose membrane, latex beads, or polystyrene beads.

The kit can include microtiter plates to which the peptide(s) of the invention have been pre-adsorbed, another appropriate assay device, various diluents and buffers, labeled conjugates or other agents for the detection of specifically bound antigens or antibodies, and other signal-generating reagents, such as enzyme substrates, cofactors and chromogens. Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex. Such kits provide a convenient, efficient way for a clinical laboratory to diagnose infection by a pathogenic *Borrelia*, such as a *B. burgdorferi*.

Another aspect of the invention is an isolated antibody, antigen-specific antibody fragment, or other specific binding partner, which is specific for a peptide of the invention, e.g., wherein said antibody, antigen-specific antibody fragment, or specific binding partner is specific for one or the peptides of the invention. Antibodies, e.g. polyclonal, monoclonal, recombinant, chimeric, humanized, single-chain, Fab, and fragments thereof, can be prepared according to any desired method. See also screening recombinant immunoglobulin libraries (e.g., Orlandi et al. (1989) *Proc. Natl. Acad. Sci. USA* 86, 3833-3837; Huse et al. (1989) *Science* 256, 1275-1281); and in vitro stimulation of lymphocyte populations (Winter et al. (1991) *Nature* 349, 293-299). The antibodies can be IgM, IgG, subtypes, IgG2a, IgG1, etc. Antibodies can be used from any source, including, goat, rabbit, mouse, chicken, etc. An antibody specific for a peptide means that the antibody recognizes a defined sequence of amino acids within or including the peptide. Other specific binding partners include, e.g., aptamers and PNA. The preparation of polyclonal antibodies is well-known to those skilled in the art. See, for example, Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992). The preparation of monoclonal antibodies likewise is conventional. See, for example, Kohler & Milstein (1975) *Nature* 256, 495; Coligan et al., sections 2.5.1-2.6.7; and Harlow et al., Antibodies: A Laboratory Manual, page 726 (Cold Spring Harbor Pub. 1988).

An isolated antibody, antigen-specific antibody fragment, or other specific binding partner of the invention can be used for a variety of applications, including therapeutic and diagnostic applications. By an "isolated" antibody is meant herein an antibody molecule that is removed from its original environment (e.g., the natural environment if it is naturally occurring), and is isolated or separated from at least one other component with which it is naturally associated. For example, a naturally-occurring antibody present in its natural living host is not isolated, but the same antibody, separated from some or all of the coexisting materials in the natural system, is isolated. Such antibodies could be part of a composition, and still be isolated in that such composition is not part of its natural environment One aspect of the invention is a method for detecting in a subject the presence of a naturally occurring antigen, itself, in its association with a pathogenic *Borrelia*, using an isolated antibody of the invention. The method can be used to determine that a subject has been exposed to, or infected by, a pathogenic *Borrelia*. In one embodiment, the method comprises contacting a sample (e.g. a bodily fluid or tissue suspected of containing a pathogenic *Borrelia*) from a subject with an antibody of the invention, under conditions effective for the formation of a specific antigen-antibody reaction. Preferably, the antibody is conventionally labeled, either directly or indirectly, for detection, e.g., with an enzyme such as HRP, avidin or biotin, chemiluminescent reagents, etc. Following the binding of the antibody to the antigen, excess labeled antibody is optionally removed, and the reaction mixture is analyzed to determine the presence or absence of the antigen-antibody complex and the amount of label associated therewith.

In one embodiment, a monoclonal or polyclonal antibody of the invention (which is capable of binding to the antigen) is bound to an ELISA plate. A sample, such as a biological fluid, is incubated on the antibody-bound plate and washed. Detection of an antigen-antibody complex and qualitative measurement of the labeled antibody are performed conventionally.

Other useful assay formats include the filter cup and dipstick. In the former assay, an antibody of the invention is fixed to a sintered glass filter to the opening of a small cap. The biological fluid or sample (e.g., about 5 mL) is worked through the filter. If the antigen is present (e.g. following infection with a pathogenic *Borrelia*), it will bind to the filter which can then be visualized through a second antibody/detector. The dipstick assay involves fixing an antigen or antibody to a filter, which is then dipped in the biological fluid, dried and screened with a detector molecule.

Kits for conducting this or other assay methods, using an antibody, antigen-specific antibody fragment, or other specific binding partner of the invention, are also included in the invention.

Much of the preceding discussion is directed to the detection of antibodies against pathogenic *Borrelia*. However, it is to be understood that the discussion also applies to the detection of primed T-cells, either in vitro or in vivo.

It is expected that a cell-mediated immune response (e.g. a T-helper response) is generated, since IgG is produced. It is therefore expected that it will be possible to determine the immunological reactivity between primed T-cells and a peptide of the invention. In vitro this can be done by incubating T-cells isolated from the subject with a peptide of the invention and measuring the immunoreactivity, e.g. by measuring subsequent T-cell proliferation or by measuring release of cytokines from the T-cells, such as IFN-.gamma; these methods are well-known in the art.

When a method of the invention is carried out in vivo, any of a variety of conventional assays can be used. For example, one can perform an assay in the form of a skin test, i.e. by intradermally injecting, in the subject, a peptide of the invention A positive skin reaction at the location of injection indicates that the subject has been exposed to and infected with a pathogenic *Borrelia* capable of causing Lyme disease, and a negative skin response at the location of injection indicates that the subject has not been so exposed/infected. This or other in vivo tests rely on the detection of a T-cell response in the subject.

Peptides, compositions comprising the peptides (such as diagnostic compositions), kits and methods of the invention offer a number of advantages. For example, they allow for simple, inexpensive, rapid, sensitive and accurate detection of Lyme disease, and avoid serologic cross-reactivity with other conditions with "Lyme-like" symptoms, such as myalgias, arthralgias, malaise or fever, including conditions such as syphilis, chronic arthritis, and multiple sclerosis. This allows for an accurate diagnosis. Furthermore, a diagnostic test of the invention (e.g. an ELISA assay or a Luminex bead based assay) is useful in serum samples that contain anti-OspA antibodies or other antibodies produced in response to a vaccine based on the outer surface proteins of *Borrelia*; the peptides of the invention do not cross-react with such antibodies, thereby allowing the differentiation of vaccinated individuals from individuals who were naturally infected with *B. burgdorferi*. In addition, the small size of a peptide of the invention allows it to be readily combined with other diagnostic peptides, described herein or known to those of skill in the art, e.g. from other *Borrelia* proteins, into a linear, multi-antigenic peptide for use in a diagnostic assay. The use of multiple peptides of the invention in a single assay (e.g. in the form of a cocktail) will increase the sensitivity of the assay for positive Lyme samples but not for the cross-reactivity controls and normal serum. By including peptides from a variety of *Borrelia* proteins, the sensitivity of an assay is greatly increased over assays in which only a single peptide, or several peptides from a single protein, are used.

Other advantages of the peptides discussed herein include that they bind well to both IgG and IgM, and are derived from antigens that are expressed early after infection.

In the foregoing and in the following examples, all temperatures are set forth in uncorrected degrees Celsius; and, unless otherwise indicated, all parts and percentages are by weight.

EXAMPLES

Example I—Identification and Characterization of Diagnostic Peptides

Methods and Materials
Patient Samples:

Lyme disease patient samples were collected under informed consent with IRB approval from the institutional review boards of the respective institutions. 104 early Lyme disease sera from collected from patients upon initial presentation with erythema migrans at Stonybrook University in Stonybrook, N.Y. (n=22), Westchester Medical Center in Westchester, N.Y. (n=32) or Gundersen-Lutheran Medical Center in La Crosse, Wis. (n=50). 20 late Lyme disease samples were collected patients with Lyme arthritis upon first clinical presentation with swollen joints (n=20) to at Gundersen-Lutheran Medical Center in La Crosse, Wis. All three regions where samples were collected are highly endemic for Lyme disease. Sera from healthy individuals (n=64) collected in New Mexico, which is non-endemic for Lyme disease, were purchased from Creative Testing Solutions (Tempe, Ariz.). 80 sera samples collected from patients with Rheumatoid arthritis (RA) (n=48) or whom had a positive Rapid Plasma Reagin (RPR+) test result (n-=39) were purchased from Bioreclamation LLC (Westbury, N.Y.). The RPR test is a first tier test for the laboratory diagnosis of Syphillis, which is caused by the spirochete *Treponema pallidum*. All RPR+ sera used in this study also tested positive or equivocal for antibodies against *T. pallidum* by ELISA (Abnova, Walnut, Calif.). Negative disease control sera were collected in areas that have Lyme disease (the northeastern United States).

Epitope Mapping and Peptides:

Epitope mapping of full-length DbpB was performed by ArrayIt, Corp. (Sunnyvale, Calif.). Briefly, an overlapping peptide library consisting of 20-AA long peptides overlapping by 15-AA (offset by 5-AA) was generated using the sequence for DbpB from *B. burgdorferi* B31 (Accession #AAC66244). The sequence submitted for mapping lacked the first 8 AA. The library was exposed to 8 sera containing antibodies against *B. burgdorferi* proteins, as determined by commercial Lyme immunostrips (Viramed Biotech AG, Planegg, Germany). IgM and IgG binding were independently evaluated, and data were reported in terms of fluorescent binding intensity. Peptides generated from epitope mapping data were produced by Lifetein, Inc (South Plainfield, N.J.). The following homologous sequences were identified using the protein BLAST algorithm on the NCBI website, DbpB: *B. burgdorferi* ia (Accession #AAM01206), *B. burgdorferi* ZS7 (Accession #AAC70021), *B. burgdorferi* JD1 (Accession #AAC70033), *B. burgdorferi* N40 (Accession #AAC70023), *B. burgdorferi* IPS (Accession #AAC70043), *B. burgdorferi* Sh-2-82 (Accession #AAC70025), *B. garinii* Far04 (Accession #YP_002477645), *B. garinii* PBr (Accession #YP_002476934), *B. garinii* 46 (Accession #AAM01204), *B. gariniiI* Nsk-10-06 (Accession #ACH73213), *B. afzelii* PKo, *B. afzelii* PGau (Accession #YP_853847), *B. afzelii* (1082) (Accession #AM1201). Sequence alignments were constructed for full-length DbpB using CLC workbench (CLC bio, Cambridge, Mass.), only the regions of the alignments corresponding to the epitopes of interest were displayed.

ELISA:

Immune reactivity to peptide antigens was confirmed by ELISA, as previously described {{820 Amaboldi, P. M. 2013}}. Briefly, 96-well plates were coated with 10 µg/ml of single peptides, or 0.5 µg/ml of recombinant protein. Sera were added at a 1:100 dilution. Antibody binding was detected by addition of a 1:8000 dilution of IgM (t-chain specific) or a 1:5000 dilution of HRP-labeled goat anti-human IgG (γ-chain specific) (Southern Biotech, Birmingham, Ala.). Data are presented as absorbance, 450 nm.

Data Analysis:

Statistical analysis was performed using using Prism 6.0 (Graphpad, La Jolla, Calif.). Statistical differences in mean absorbance of antibody binding to peptide or protein were determined using a Kruskal-Wallis nonparametric test, followed by a Dunn's multiple comparison test. Sensitivity and specificity of each peptide was calculated via ROC analysis comparing IgM and IgG binding in Lyme patient sera with negative controls. The cut-off value used for comparing sensitivity and specificity was 3 SD from the mean of healthy controls. Statistical analysis of categorical data presented in tables and the text was performed using a Chi square analysis.

Results

Linear epitope mapping of DbpB was accomplished by probing overlapping peptide libraries containing full length sequences derived from the B31 strain of *B. burgdorferi* sensu stricto, with serum obtained from 8 Lyme disease patients with high levels of anti-*Borrelia* antibody as determined using commercially available Lyme disease immunoblot strips. Sera were considered high titer if 9-10 out of 10 well-defined bands were clearly identifiable in the immunostrip analysis. Each patient serum sample bound to multiple different sequences in the peptide library. The epitope mapping protocol used for DbpB differentiated between IgM and IgG binding. $DbpB_{(38-67)}$ was comprised of two overlapping peptides, DbpB(38-57) which was bound by IgM in 100% of the samples and DbpB(48-67) which was bound by IgG in 100% of the samples (FIG. 2). Numerous other DbpB peptides that were bound by antibody in some, but not all, patient serum samples were excluded from further analysis.

Peptide based diagnostics are entirely dependent upon antibody recognition of linear AA sequences within a protein. Therefore, the efficacy of a peptide based diagnostic assay is contingent upon the target sequence being highly conserved among disease causing bacteria, as a variations of that sequence would give rise antibodies that do not bind the assay target resulting in false negatives. DbpA has been described as having a high degree of sequence variability among the different species of disease causing *Borrelia*, while DbpB is believed to be less variable. We aligned the full length sequence of DbpB from *B. burgdorferi* B31 with sequences derived from multiple strains of *B. burgdorferi, B. garinii*, and *B. afzelii* using the NCBI protein BLAST algorithm, and assessed variances in the amino acid sequences of the epitopes identified in our epitope mapping experiments (FIG. 2). There was a high degree of variability observed in epitope sequences from and DbpB among the different strains of *Borrelia*. However, these differences, from the amino acid sequence used in our epitope mapping, *B. burgdorferi* B31, were principally observed between different pathogenic isolates of *B. burgdorferi, B. garinii*, and *B. afzelii*. Within individual strains, there was a high degree of sequence conservation (FIG. 2). These data indicate that limited sequence variability exists in DbpA and DbpB sequences among strains in the US. As such, the linear peptide epitope identified here could be successful in surveying the US population for infected individuals.

To test the efficacy of $DbpB_{(38-67)}$ as a target for a diagnostic assay for Lyme disease, peptides were incubated with panels of sera from patients with erythema migrans (early Lyme disease), lyme arthritis (LA, late Lyme disease), rheumatoid arthritis (RA), syphilis (RPR+), and healthy individuals, and compared to binding with their respective 'parent' rDbp. Early Lyme disease serum was collected from patients upon their initial clinical presentation with an erythema migrans skin lesion in an endemic region. RPR+ sera were used as negative controls for potential cross-reactive antibody raised against a related spirochete, *Treponema pallidum*. Rheumatoid arthritis sera were used as a negative control for chronic inflammation marked by high antibody levels and joint damage, which can occur in Lyme disease. The peptide binding efficacy of both IgM and IgG was independently evaluated in patient sera because erythema migrans can appear as early as 3 days following tick bite, which is well before the development of a detectable IgG response. Additionally, as each peptide has its own inherent level of cross-reactivity, individual cutoffs were established for each peptide by determining the mean absorbance of IgM and IgG binding in healthy control sera and calculating values for 3× the standard deviation (positive cutoff) and 2× the standard deviation (equivocal cutoff).

rDbpB and $DbpB_{(38-67)}$ were, individually, somewhat more effective at detection of IgM and IgG antibody in early Lyme disease sera compared to their DbpA counterparts. rDbpB and $DbpB_{(38-67)}$ positively detected IgM in 37.9% (39/103) and 41.7% (43/103), and IgG in 51.9% (54/104) and 23.1% (24/104) of early Lyme disease serum samples, respectively (FIG. 1 and Table 2). IgM recognition of both protein and peptides was significantly higher in early Lyme disease sera compared to negative controls (p<0.05). On the other hand, positive detection of IgG binding to peptides was only significantly higher when comparing early Lyme sera to healthy controls and RA sera (p<0.01), but not when compared to RPR+ sera. Positive binding of antibody to rDbpB was not significantly higher than binding to DbpB6. If the total number of patient samples positive for either IgM or IgG binding were considered, then recognition of rDbpB and $DbpB_{(38-67)}$ improved to 61.5% (64/104) and 48.0% (50/104) in early Lyme disease samples, respectively (Table 3), and was significantly higher than antibody binding in negative control sera (p<0.01). Cross reactivity was not significantly different between protein and peptides. rDbpB and $DbpB_{(38-67)}$ bound to either IgM or IgG in 3.1% (2/64) and 4.7% (3/64) of healthy control sera, 6.5% (3/48) and 0% (0/48) of RA sera, and 12.5% (4/32) and 6.3% (2/32) of RPR+ sera, respectively (FIG. 1 and Tables 2 and 3).

TABLE 2

DbpB peptide and protein serum IgM and IgG binding

| | | IgM | | | | | IgG | | | | |
|---|---|---|---|---|---|---|---|---|---|---|---|
| | | Early Lyme[d] | Normal | RA | RPR+ | Late Lyme[e] | Early Lyme[d] | Normal | RA | RPR+ | Late Lyme[e] |
| DbpB6 | Pos[a] | 42.7.0% | 3.1% | 0.0% | 0.0% | 5.0% | 23.0% | 1.6% | 0.0% | 6.3% | 5.0% |
| | | (43/103) | (2/64) | (0/46) | (0/32) | (1/20) | (24/104) | (1/64) | (0/46) | (2/32) | (1/20) |
| | Equiv[b] | 11.6% | 1.6% | 4.3% | 0.0% | 5.0% | 8.7% | 0.0% | 8.7% | 15.6% | 10.0% |
| | | (12/103) | (1/64) | (2/46) | (0/32) | (2/20) | (9/104) | (1/64) | (4/46) | (5/32) | (2/20) |
| | Neg[c] | 46.6% | 95.3% | 95.7% | 100.0% | 90.0% | 68.3% | 98.4% | 91.3% | 78.1% | 85.0% |
| | | (48/103) | (61/64) | (44/46) | (32/32) | (18/20) | (71/104) | (63/64) | (42/46) | (25/32) | (17/20) |
| rDbpB | Pos[a] | 37.8% | 1.6%% | 0.0% | 0.0% | 0.0% | 51.9% | 1.6% | 6.5% | 3.1% | 95% |
| | | (39/103) | (1/64) | (0/46) | (0/32) | (5/20) | (54/104) | (1/64) | (3/41) | (1/32) | (19/20) |
| | Equiv[b] | 12.6% | 3.1% | 0.0% | 3.1% | 10.0% | 3.8% | 1.6% | 4.3% | 6.3% | 0% |
| | | (13/103) | (2/64) | (0/46) | (1/32) | (2/20) | (4/104) | (1/64) | (2/46) | (2/32) | (0/20) |
| | Neg[c] | 49.5% | 95.3% | 100.0% | 96.8% | 90.0% | 44.2% | 96.8% | 89.1% | 90.6% | 5.0% |
| | | (51/103) | (61/64) | (46/46) | (31/32) | (18/20) | (46/104) | (62/64) | (41/46) | (29/32) | (1/20) |

[a]Positive - More than 3 SD from mean of healthy controls
[b]Equivocal - Between 2 SD and 3 SD from mean of healthy controls
[c]Negative - Less than 2 SD from the mean of the health controls
[d]Early Lyme = Erythema migrans positive
[e]Late Lyme = Lyme arthritis

TABLE 3

DbpB peptide and protein serum IgM + IgG binding

| | | Total Antibody[f] | | | | |
|---|---|---|---|---|---|---|
| | | Early Lyme[d] | Normal | RA | RPR+ | Late Lyme[e] |
| DbpB6 | Pos[a] | 48.1% | 4.7% | 0% | 6.3% | 10.0% |
| | | (50/104) | (3/64) | (0/46) | (2/32) | (2/20) |
| | Equiv[b] | 12.5% | 1.6% | 10.9% | 15.6% | 15.0% |
| | | (13/104) | (1/64) | (5/46) | (5/32) | (3/20) |
| | Neg[c] | 39.4% | 93.8% | 89.1% | 78.1% | 75.0% |
| | | (41/104) | (60/64) | (41/46) | (25/32) | (15/20) |
| rDbpB | Pos[a] | 61.5% | 3.1% | 6.5% | 6.3% | 95.0% |
| | | (64/103) | (2/64) | (3/46) | (2/32) | (19/20) |
| | Equiv[b] | 4.8% | 3.1% | 4.3% | 9.4% | 0.0% |
| | | (5/103) | (2/64) | (2/48) | (3/32) | (0/20) |
| | Neg[c] | 33.7% | 93.8% | 89.0% | 84.4% | 5.0% |
| | | (35/103) | (60/64) | (41/46) | (27/32) | (1/20) |

[a]Positive - More than 3 SD from mean of healthy controls
[b]Equivocal - Between 2 SD and 3 SD from mean of healthy controls
[c]Negative - Less than 2 SD from the mean of the health controls
[d]Early Lyme = Erythema migrans positive
[e]Late Lyme = Lyme arthritis
[f]Total Antibody = the total number of samples that contained either IgM, IgG, or both antibodies binding to target peptides or recombinant proteins To test the diagnostic potential of Dbp peptides in the detection of disseminated late Lyme disease, we obtained sera from patients diagnosed with Lyme arthritis at the time they first presented with swollen joints. Lyme arthritis is the most common manifestation of disseminated late Lyme disease observed in North America. DbpB$_{(38-67)}$ was not efficient as a diagnostic targets in Lyme arthritis patients. On the other hand, antibodies to rDbpB were identified in 95% of the late Lyme disease (19/20) samples; the same patient sample was negative for both proteins (FIG. 1, Tables 2 and 3).

Figure 3A:
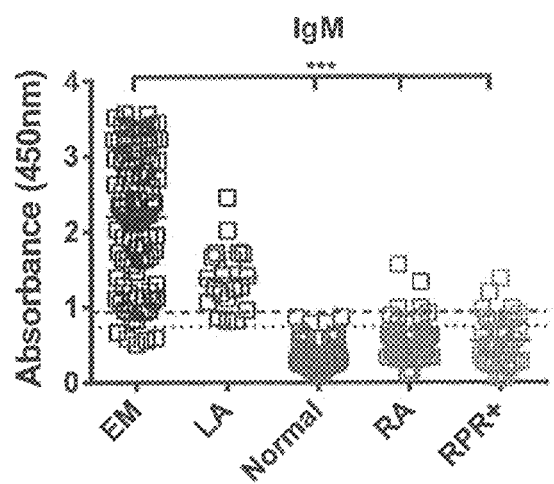
FIG. 3a shows serum IgM (upper panel) binding of DbpA(16-30)-DbpB(38-67) in serum from patients with early Lyme disease (EM, erythema migrans) (n=96), late Lyme disease (LA, Lyme arthritis) (n=20), healthy controls (normal) (n=64), rheumatoid arthritis (RA) (n=48), or Syphilis (RPR+) (n=32). The dashed line represents the cutoff for positive binding, 3SD from the mean of healthy controls. The dotted line represents the cutoff for equivocal binding, 2SD from the mean of healthy controls. *$p<0.001$
Figure 3B:
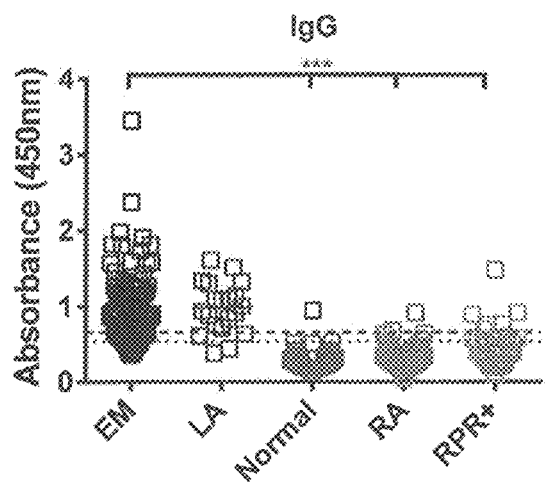
FIG. 3b shows serum IgG (lower panel) binding of DbpA(16-30)-DbpB(38-67) in serum from patients with early Lyme disease (EM, erythema migrans) (n=96), late Lyme disease (LA, Lyme arthritis) (n=20), healthy controls (normal) (n=64), rheumatoid arthritis (RA) (n=48), or Syphilis (RPR+) (n=32). The dashed line represents the cutoff for positive binding, 3SD from the mean of healthy controls. The dotted line represents the cutoff for equivocal binding, 2SD from the mean of healthy controls. *$p<0.001$

The central hypothesis driving the development of a multi-peptide based diagnostic assay is that multiple peptides of high specificity can be included in a single assay to enhance sensitivity without sacrificing specificity. To test this hypothesis, we assessed the efficacy of a diagnostic assay combining a single DbpA peptide, DbpA$_{(16-30)}$, with a single DbpB peptide, DbpB$_{(38-67)}$. These peptides were chosen because they each detected the highest number of IgM and IgG positive sera for their respective protein. The combination of DbpA$_{(16-30)}$-DbpB$_{(38-67)}$ detected IgM in 91.7% (88/96), and IgG in 76.0% (73/96) of early Lyme disease serum samples (FIG. 3). Of the 96 early samples, either IgM or IgG to the DbpA$_{(16-30)}$-DbpB$_{(38-67)}$ target antigen was detected in 94.8% (91/96) and the remaining 5.2% (5/96) were equivocal with no false negative samples. A similar increase was observed in late Lyme disease sera, where positive detection of antibody increased to 90% (18/20) with 10% (2/20) of samples being equivocal and no false negatives (FIG. 3). Nonspecific binding of IgM or IgG antibody in healthy control (1.6% (1/64)) and RA (10.4% (5/48)) sera was similar to levels observed for single peptides. However, nonspecific serum IgM and IgG binding of RPR sera to the duel target peptides was significantly elevated compared to single peptides (28.1% (9/32) vs. 9.4% (3/32) for DbpA$_{(16-30)}$ and 6.3% (2/32) for DbpB$_{(38-67)}$) ($P<0.05$).

A. Materials and Methods

The following methods can be used for the experiments in the following Examples.

1. Peptide Synthesis:

For the epitope mapping studies, synthetic peptides were custom synthesized by the commercial facility, ProImmune (Oxford, England), under the direction of the inventors, using conventional procedures. For each of 10 B. burgdorferi proteins, a complete library was generated, consisting of peptides of 15 amino acids, offset by 5 amino acids, i.e. overlapping by 10 amino acids. We provided the sequences of each protein for which a peptide library was generated, specifically: Borrelia membrane protein A (BmpA), Decorin-binding protein B (DbpB), flagellar basal body-associated protein (FlilB), oligopeptide ABC transporter II (OppA), BBG33 (putative uncharacterized protein) (Bbg33), outer-surface-protein C type K (OspC typeK), integral outer membrane protein p66 (p66), recombinase A (RecA), outer-surface-protein C type A (OspC type A), and lipoprotein LA7 (LA-7).

Significant binding was demonstrated for multiple peptides within each of the proteins that were submitted for analysis. We chose the individual peptides in Table 1 based upon their ability to bind more than 75% of the serum samples, bind to the serum samples at multiple dilutions (indicating high affinity binding), and a low sequence identity with other bacterial species as determined by sequence alignment using the NCBI protein BLAST algorithm on the NCBI website (we chose peptides unique to *Borrelia* species).

2. Test Panels of Sera

For the initial evaluation of the peptides including identified diagnostic epitopes, we had Lifetein (South Plainfield, N.J., 07080) generate peptides containing the epitope. In our initial characterization, we utilized sera from nine patients who had microbiologically (by culture) confirmed Lyme disease. These patients had a positive serologic response demonstrated by western blot, using the current prescribed methods for the laboratory diagnosis of Lyme disease The patients had early Lyme disease.

For further characterization of the peptides, e.g., to determine specificity and sensitivity, we use panels of sera, including sera from a defined number of patients with PCR-confirmed early Lyme disease. The Lyme serum panels are representative of the population of suburban New York and include samples from adults males, females, whites and minorities, reporting to the Lyme disease clinic at Westcheseter Medical Center (Westchester, N.Y.). Lyme disease was confirmed in these patients by PCR (PCR+) or by culture. Sera from normal healthy individuals with neither a known history of Lyme disease nor immunoblot patterns characteristic of the infection obtained from areas endemic and non-endemic for LD are used as negative healthy controls. Serum from patients with Syphilis, rheumatoid arthritis, systemic lupus erythematosus, and *Helicobacter pylori* infection are used as negative controls for cross-reactivity with antibodies raised in response to other diseases (cross-reactivity controls). These serum samples, as well as the negative controls, have been purchased from Bioreclamation, LLC (Westbury, N.Y.).

B. Linear Epitope Mapping of B-Cell Epitopes:

Linear mapping of B-cell epitopes of candidate *B. burgdorferi* proteins was carried out by ProImmune, under the direction of the inventors. A more detailed discussion of the epitope mapping procedure is described on the ProImmune world wide website, at promiimue.com. Briefly, the peptides described above were distributed in a high density microarray format. Each peptide was screened for binding with the eight sets of sera described above, and with appropriate control sera for specificity and sensitivity, as described above. The peptides were ranked with regard to the strength of their binding to the sera.

We chose the individual peptides in table 1 based upon three criteria:

1) their ability to bind at least 75% (6/8) of the serum samples, 2) their ability to bind to multiple (~50%) of the serum samples at multiple dilutions (indicating high affinity binding), 3) low sequence identity with other bacterial species as determined by sequence alignment using the NCBI protein BLAST algorithm on the NCBI website (we chose peptides unique to *Borrelia* species, and had less than a 50% sequence identity with peptides from other bacteria).

C. Further Characterization of Candidate Peptides, to Determine Specificity and Sensitivity.

ELISA Procedure

Solutions of purified peptides (and control proteins) in 100 mM BIS-TRIS propane buffer (pH9.7) are used to coat commercial microwell plates (MaxiSorp®, Nunc) at 10 μg/ml. The coating procedure is as follows: 50 μl of a solution containing the appropriate concentration of antigen is added to each well and the microwell plate incubated either for 1 h at room temperature or overnight at 4° C. The antigen solution is removed from the wells; the plate washed three times with phosphate buffered saline containing 0.05% Tween-20, pH 9 (PBST); and 300 μl of a conventional blocking solution (e.g., 100 mM PBS pH7.4, 5% fetal bovine serum) added. The standard blocking protocol successfully saturates this high antigen binding capacity, leaving low background readings in the control channels. A protein concentration of about 10 μg/ml in the coating buffer is optimal. Following a 60-minute incubation at room temperature, the plates are washed three times with PBST buffer. Although the amount of each peptide bound to the surface and the amount of any one epitope exposed to the solution varies somewhat, the amount of bound epitope is not limiting within the useful range of the ELISA.

A standard procedure for the ELISA tests is employed. For example, human sera is serially diluted (1:2), starting at a 1:50 dilution in 50 μl of blocking buffer. The samples are added in each well and the plate is incubated for 2 h at room temperature. Plates are washed three times with PBST buffer. The horseradish peroxidase conjugated anti-human IgG (H+L) (Jackson ImmunoResearch, West Grove, Pa.) antibody is diluted at 1:15,000 in blocking buffer; 100 ul of this solution is dispensed onto the plate and incubated for 30 minutes at room temperature. Plates are washed three times with TBST buffer and 100 ul of substrate is added (pNPP Microwell Substrate System, KPL, Gaithersburg, Md.) and incubated for 1 h at room temperature. Plates are read at 405 nm on a microplate reader (Molecular Devices, Spectramax 320).

Immobilization of Biotinylpeptide-Streptavidin Conjugates in an ELISA Format.

Biotinylpeptide-Strepavidin conjugates in sodium phosphate buffer are used to coat microwell plates (MaxiSorpo, Nunc). The coating procedure is as follows: antigen is added to each well and the microwell plate incubated either for 1 h at room temperature or overnight at 4 C. The antigen solution is removed from the wells, the plate washed three times with PBS, and 200 ul of blocking solution (2% bovine serum albumin fraction V (Sigma) in PBS added. Following a 30 min incubation at 37 C, the plates are washed three times with PBS, wrapped in plastic and stored at 4° C. until used. The binding of the peptides is monitored by ELISA using monoclonal antibodies specific for a control chimeric protein that is coated as Biotinylprotein-Strepavidin. A protein concentration of about 5 ug/ml in the coating buffer is optimal.

Sensitivity and Specificity

Peptide libraries were generated for each of the protein antigens described above consisting of 15-mer peptides overlapping by 10 amino acids. 8 serum samples from patients with culture confirmed Lyme disease that demonstrated seropositivity by western blot were used to screen the different peptide libraries. Four dilutions of antibody were incubated with the libraries using ProImmune's proprietary REVEAL epitope mapping system. Positive binding was reported for several peptides in each protein. Individual peptides were chosen for further analysis using three criteria:

1) their ability to bind at least 75% (6/8) of the serum samples, 2) their ability to bind to multiple (~50%) of the serum samples at multiple dilutions (indicating high affinity binding), 3) low sequence identity with other bacterial species as determined by sequence alignment using the NCBI protein BLAST algorithm on the NCBI website (we chose peptides unique to *Borrelia* species, and had less than a 50% sequence identity with peptides from other bacteria).

The peptides selected are listed in Table 1.

Each of these peptides was then further screened in an ELISA assay, using serum samples from nine patients with confirmed seropositivity for Lyme disease by western blot, ten healthy individuals with no history of Lyme disease (negative control), and nine patients with confirmed syphilis (RPR+, control for cross-reactivity), as described above. A sample was considered positive if a statistically significant difference in the mean binding of serum antibodies from patients with serologically confirmed Lyme disease was present compared to serum from patients confirmed to be sero-negative for Lyme disease (normal controls), and serum from patients that are positive for Syphilis (RPR+), where significance is measured as $p<0.05$ as determined using a Kruskal-Wallis test followed by a Dunn's comparison test. RPR+ serum is used as a negative control because it is a disease caused by a different Spirochete pathogen (*Treponema pallidum*) which may contain antigens that are cross-reactive with *Borrelia* infected patients. Serum antibody binding was compared at single dilutions (1:100), multiple dilutions (analysis of antibody binding curves), as well as reciprocal 50% binding titers (several dilutions of each serum sample were prepared and incubated with each peptide; the 50% binding titer was determined as the dilution of antibody at which the absorbance measured in the ELISA assay had reached 50% of the maximum absorbance recorded for any of the dilutions). Representative data for antibody binding is shown in FIGS. 1-4. FIG. 2 shows the serum antibody-binding curves for 7 potential peptide antigens, demonstrating increased binding of serum from Lyme disease patients at several dilutions of the serum samples compared to serum from patients with Syphillis (RPR+) or normal control sera. FIG. 3 shows the analysis of peptide binding at a single dilution, which is more representative of the data that would obtained in a clinical laboratory setting (statistically significant differences between groups are shown by the lines and asterisks, *$p<0.05$ and $p<0.01$). FIG. 4** is a different kind of analysis which assesses the binding of serum to peptides using 50% binding titers (the dilution at which the absorbance reaches 50% of the maximal absorbance recorded for any of the dilutions). The clearly demonstrate an enhanced binding of peptides in sera from patients with Lyme disease compared to syphilis patients and/or sera from normal individuals.

Similar data have been generated for all of the peptides shown in Table I.

Multipeptide Assays

The next step is to create a multi-peptide assay using different combinations of the peptides in Table 1. Various combinations of peptides, based upon their results in single ELISAs will be combined and screened using sera from early Lyme disease patients in whom disease has been confirmed by PCR, and comparing the binding efficacy to serum from normal healthy individuals with neither a known history of Lyme disease nor immunoblot patterns characteristic of the infection obtained from areas endemic and non-endemic for LD are used as negative healthy controls. Serum from patients with Syphilis, rheumatoid arthritis, systemic lupus erythematosus, and *Helicobacter pylori* infection will be used as negative controls for cross-reactivity with antibodies raised in response to other diseases (cross-reactivity controls). The use of multiple peptides in a single assay will increase the sensitivity of the assay for positive Lyme samples but not for the cross-reactivity controls and normal serum. A cutoff of 3SD above the mean of the control groups will be used as a marker of positivity.

D. Evaluating the Ability of Peptides Containing Epitopes as Identified in Section C to Bind Anti-*B. burgdorferi* IgM and IgG Antibodies We will use serum and isolated IgG and IgM from patients with culture confirmed early LD to assess the diagnostic potential of the 21 peptides shown in Table 1. The peptide synthesis and ELISA methods that we will use are described in Example I. We expect that it is unlikely that only a single one of the peptides will provide sufficient sensitivity to identify individuals with antibodies to *B. burgdorferi* proteins. We plan to assess a variety of combinations of the epitope-containing peptides. We will use 50 serum samples from patients with culture confirmed early LD, 50 serum samples from patients with culture confirmed acute disseminated LD, 50 serum sample from patients with late LD, 50 serum from a bank of normal health patients from endemic and non endemic areas, and panels of serum from other tick borne and diseases that are in the differential diagnosis of LD. These latter panels will include serum from 20 patients with rheumatoid arthritis, 20 patients with SLE, 20 patients with syphilis, 20 patients with MS, 20 patients with *H. pylori,* 20 patients with culture confirmed HGE and 20 patients with microbiologically confirmed babesiosi.

E. Developing an Immunodiagnostic Peptide Assay

1. Selection of the Peptides:

the selection will be based on 1) additional tests of the sensitivity and specificity of each peptide (e.g. using sera from patients who have been infected with other organisms known to have cross-reactivity with *B. burgdorferi*); 2) the relative coating efficiency of each peptide combination (see below).

2. Preparation and Testing of Microwells Coated with Peptides.

We have found, unexpectedly, that the peptides of the invention are adsorbed to microwell surfaces quite well without the need for biotinylation and linking to streptavidin, and that the directly adsorbed peptides were as efficient as the streptavidin-conjugated antigens for ELISA detection of *B. burgdorferi* antibodies. The free peptides were not, however, well adsorbed on nitrocellulose surfaces for use in Fast Format (lateral flow) immunoassays. We found that direct biotinylation of synthetic peptides at the N-terminus during solid-phase synthesis was much more convenient than linking biotinyl groups to free peptides after deprotection and cleavage from the solid supports. Also, streptavidin conjugates of N-biotinylated peptides worked as well in the Rapid Format assays as did the peptides linked to streptavidin according to the published protocol (Liang et al. (1999a) (supra). Since we will synthesize some small peptides encompassing single linear epitopes, in general all peptides will be synthesized with N-terminal biotinyl residues and streptavidin conjugates will be used for both ELISA and Rapid Format (membrane) assays. With the biotinyl groups attached during the solid phase synthesis, conjugation with streptavidin is hardly more complicated than coating plates with free peptides, and there will be no worry about poor adhesion of short peptides to the immobilizing surfaces. The peptides do not need to be immobilized in a specific ratio to one another, but enough of each peptide must be bound to ensure that none of the epitopes becomes limiting in ELISA assays of patient sera.

3. Comparison of Prototype Peptide Assay to Whole *B. burgdorferi* ELISA and Western Blot.

Once we have identified the best peptide combination(s), we will compare the prototype peptide assay to the standard CDC recommended protocol. The clinical samples will be run on a standard ELISA using whole low passage *B. burgdorferi* and on IgM and IgG western blots to compare the results of the peptide assay.
Positive Controls: Recombinant proteins OspC, FlaB, DbpA and peptides of IR6 will be used as controls. The reactivity of each of the peptides will be compared to the corresponding recombinant protein.

Negative Controls: To assess non-specific binding of antibodies in our peptide assay we will use a specifically designed random peptide. To assess non-specific binding of antibodies in our recombinant protein positive control assay we will use BSA.

Positive serum samples to be used to assess peptide preparations and comparative proteins:

a. 100 serum samples obtained at presentation from patients with culture confirmed early local LD.
b. 100 serum samples obtained at presentation from patients with culture confirmed acute disseminated LD.
c. 100 serum sample from patients with late LD.

Negative control serum samples to be used to assess peptide preparations and comparative proteins:

a. 50 sera from a bank of normal health patients from endemic areas.
b. 50 sera from a bank of normal health patients from non-endemic areas.
c. 30 sera samples from individual patients with culture confirmed HGE.
d. 20 sera samples from individual patients with microbiologically confirmed babesiosis.
e. 30 sera samples from individual patients with rheumatoid arthritis
f. 30 sera samples from individual patients with SLE.
g. 20 sera samples from individual patients with syphilis.
h. 20 sera samples from individual patients with MS.
i. 20 sera samples from individual patients with *H. pylori.*

It is expected that the peptides tested will provide a sensitive, specific assay which is at least as effective as the presently approved C6 assay.

F. Preparation and Characterization of Multi-Epitope Polypeptides

In order to significantly increase the sensitivity of peptide assays based on the individual peptides described herein, we will construct multimeric peptides (dimers, trimmers and more) containing various combinations of the 21 peptides shown in Table 1 or active variants thereof. Spacers of, for example, 3 glycines will be inserted between the epitopes in the multimer. Other diagnostic peptides described herein, or known to those of skill in the art, can also be combined with peptides of the invention in multimers.

We will use the panel of 8 well defined clinically characterized and culture positive Lyme disease sera that were previously tested by ELISA: two low, two medium and two high titer from six different Lyme patients, in addition to one negative control obtained from an healthy individual.

It is expected that some combinations of the peptides of the present invention will exhibit increased sensitivity compared to the individual peptides.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional Application 61/912,675, filed Dec. 6, 2013, and in the figures, are hereby incorporated in their entirety by reference, particularly with regard to the disclosure for which they are referenced.

We claim:

1. A composition comprising a linked peptide, comprising
   (a) a first peptide KDLKNKILKIKKEATGKGVLFEAF-TGLKTG (SEQ ID NO: 1), or an active variant thereof wherein one or more of the amino acids of SEQ ID NO: 1 is substituted with an amino acid replacement, wherein the peptide or active variant specifically binds to an antibody against a pathogenic *Borrelia;* covalently linked by a peptide linker to
   (b) at least one additional peptide that specifically recognizes an antibody against the same or a different protein of the same or a different pathogenic *Borrelia;* and
   wherein the linked peptide is selected from the group consisting of:

(SEQ ID NO: 6)
   KDLKNKILKIKKEATGKGVLFEAFTG
   LKTGGGMKKNDQIVAAIALRGVA, (SEQ ID NO: 7)
   KDLKNKILKIKKEATGKGVLFEAFTG
   LKTGGGGPFILEAKVRATTVAE, (SEQ ID NO: 8)
   KDLKNKILKIKKEATGKGVLFEAFTG
   LKTGGGNKTFNNLLKLTILVNGGGTI
   LVNLLISCGLTGA, (SEQ ID NO: 9)
   KDLKNKILKIKKEATGKGVLFEAFTG
   LKTGGGGNKTFNNLLKLTILVN, (SEQ ID NO: 10)
   DNVKNKILQIKEEAAKKGVNFKAFTG
   TATGGGMKKNDQIVAAIALRGVA, (SEQ ID NO: 11)
   DNVKNKILQIKEEAAKKGVNFKAFTG
   TATGGGGPFILEAKVRATTVAE, (SEQ ID NO: 12)
   DNVKNKILQIKEEAAKKGVNFKAFTG
   TATGGGGNKTFNNLLKLTILVNGGGT
   ILVNLLISCGLTGA

-continued (SEQ ID NO: 13)
KDVKNKILQIKKDAEDKGVNFAAFTS

SETGGGGMKKNDQIVAAIALRGVA, (SEQ ID NO: 14)
KDVKNKILQIKKDAEDKGVNFAAFTS

SETGGGGPFILEAKVRATTVAE,
and (SEQ ID NO: 15)
KDVKNKILQIKKDAEDKGVNFAAFTS

SETGGGNKTFNNLLKLTILVNGGGTI

LVNLLISCGLTGA, or an active variant thereof wherein one or more of the amino acids in the linked peptide is substituted with an amino acid replacement, whereby both peptides in the linked peptide specifically bind to an antibody against a pathogenic *Borrelia*.

2. A diagnostic reagent comprising a composition of claim 1 and a detection system for detecting the peptide, and/or a substrate for immobilizing the peptide.

3. A kit for diagnosing Lyme borreliosis, comprising a composition of claim 1 and a detection system for detecting the peptide bound to an antibody to a pathogenic *Borrelia* protein and/or a substrate for immobilizing the peptide.

4. A method for diagnosing Lyme disease in a subject, comprising contacting a sample from a subject suspected of having antibodies against a causative agent of Lyme disease with a composition of claim 1, conditions effective for the formation of a peptide-antibody complex, and detecting the presence of the peptide-antibody complex.

5. The method of claim 4, wherein the peptide-antibody complex is detected by adding a binding partner which is labeled, or which can be labeled with a signal generating reagent.

6. The method of claim 5, wherein the binding partner is an antibody attached to an enzyme, and a signal is generated when the enzyme reacts with a suitable substrate.

7. The method of claim 4 wherein the detecting is performed with an ELISA assay.

8. The method of claim 4, wherein the detecting is performed by immobilizing the peptides onto beads with a unique spectral signature.

9. The method of claim 4, wherein the subject is a cat or a dog.

10. The method of claim 4, wherein the subject is a human.

11. The composition of claim 1, wherein the linked peptide is selected from the group consisting of SEQ ID NOs 6-15.

* * * * *